United States Patent [19]

Hanisch et al.

[11] Patent Number: 5,643,566
[45] Date of Patent: Jul. 1, 1997

[54] FORMULATION PROCESSES FOR LIPOPHILIC PROTEINS

[75] Inventors: Wolfgang H. Hanisch, Balmoral Heights, Australia; Pete M. Fernandes, Walnut Creek, Calif.; Terrance Taforo, Oakland, Calif.; James W. Thomson, Albany, Calif.

[73] Assignee: Cetus Corporation, Emeryville, Calif.

[21] Appl. No.: 474,769

[22] Filed: Jun. 7, 1995

Related U.S. Application Data

[62] Division of Ser. No. 266,832, Jun. 28, 1994, which is a continuation of Ser. No. 865,411, May 7, 1992, abandoned, which is a continuation of Ser. No. 923,425, Oct. 27, 1986, abandoned, which is a continuation-in-part of Ser. No. 775,751, Sep. 13, 1985, Pat. No. 4,992,271, which is a continuation-in-part of Ser. No. 752,403, Jul. 5, 1985, abandoned, which is a continuation-in-part of Ser. No. 592,077, Mar. 22, 1984, abandoned, which is a division of Ser. No. 495,896, May 18, 1983, Pat. No. 4,462,940, which is a continuation-in-part of Ser. No. 422,421, Sep. 23, 1982, abandoned.

[51] Int. Cl.⁶ .......................... A61K 38/20; A61K 38/21
[52] U.S. Cl. .................. 424/85.4; 424/85.6; 424/85.2; 530/351
[58] Field of Search .................. 424/85.6, 85.4, 424/85.2; 530/351

[56] References Cited

U.S. PATENT DOCUMENTS

| | | | |
|---|---|---|---|
| 4,359,389 | 11/1982 | Heine | 424/85.6 |
| 4,364,863 | 12/1982 | Leibowitz et al. | 530/351 |
| 4,415,852 | 11/1983 | Leibowitz et al. | 324/436 |
| 4,440,679 | 4/1984 | Fernandes et al. | 530/363 |
| 4,462,940 | 7/1984 | Hanisch et al. | 530/351 |
| 4,588,585 | 5/1986 | Mark et al. | 424/85.6 |
| 4,645,830 | 2/1987 | Yasushi et al. | 530/351 |
| 4,647,454 | 3/1987 | Cymbalista | 424/85.6 |
| 4,659,570 | 4/1987 | Terano | 424/85.5 |
| 4,675,184 | 6/1987 | Gaseyawa et al. | 424/85.4 |
| 4,680,175 | 7/1987 | Estes | 424/85.4 |
| 4,714,611 | 12/1987 | Yasabrivgo et al. | 424/85.5 |
| 4,992,271 | 2/1991 | Fernandes et al. | 424/85.2 |

FOREIGN PATENT DOCUMENTS

| | | |
|---|---|---|
| 0042246 | 12/1981 | European Pat. Off. . |
| 0089245 | 9/1983 | European Pat. Off. . |
| 0133767 | 3/1985 | European Pat. Off. . |
| 59-181224 | 10/1984 | Japan . |

OTHER PUBLICATIONS

Windholz, et al., The Merck Index, p. 644, monograph 4347 (1983).
R. Derynck, Nature, "*Expression of Human Fibroblast Interferon Gene in Escherichia coli*", vol. 287, pp. 193–197 (Sep. 18, 1980).
Sedmak, et al., Methods in Enzymology, "*Procedures for Stabilizatin of Interferons*", vol. 78, pp. 591–595 (1981).
E. Gross, et al., The Peptides, pp. 39–41 (1983).
Edy, et al., Pro. Soc. Exp. Biol. & Med., vol. 146, pp. 249–253 (1974).
Frank, et al., J. Gen. Virol., vol. 53, pp. 389–392 (1981).
Noda, et al., CA, vol. 102 (1985), No. 154791v.
Hasigawa, et al., CA, vol. 99, No. 76904m.
Kato, et al., CA, vol. 102 (1984), No. 12428h.
Billiau, et al., Antimicrobial Agents and Chemotheraspy, vol. 16(1), pp. 49–55 (1979).

*Primary Examiner*—John Ulm
*Assistant Examiner*—Prema Mertz
*Attorney, Agent, or Firm*—Millen, White, Zelano & Branigan, P.C.

[57] ABSTRACT

Highly stable, pharmaceutical compositions comprising a therapeutically effective amount of a biologically active recombinant lipophilic protein such as human β-interferon and interleukin-2 dissolved in a non-toxic, inert, therapeutically compatible aqueous-based carrier at pH ranges of from about 6.8 to 7.8 and about 8.5 to 10, which formulations contain a stabilizer for the protein selected from the group comprising human serum album, human serum albumin and dextrose or human plasma protein fraction, and at a pH range of from about 2 to 4, which latter formulations optionally contain a carbohydrate and/or protein stabilizer, are disclosed. Further, preferred formulation processes to prepare said compositions are described which avoid highly alkaline conditions.

21 Claims, 4 Drawing Sheets

FIG. 1

IL-2 PROCESS

| | |
|---|---|
| Fermentation | |
| Cell concentration | |
| Cell wall and membrane disruption | distilled water |
| Diafiltration | 5 mM EDTA |
| Redisruption | 2 mM EDTA 1% octanol (v/v) |
| Sucrose suspension | 15–35% sucrose (w/w) |
| Centrifugation | 10,000–20,000 × g |
| Paste solubilization | 5% SDS, phosphate buffered saline |
| Centrifugation | 25,000–35,000 × g |
| Reduction | 5% SDS, 50 mM DTT, 2 mM EDTA pH 8.5 at 50°C for 20 minutes |
| Sephacryl® S200 column | 50 mM acetate, pH 5.5, 0.1% SDS, 1 mM EDTA |
| Oxidation | Protein : $CuCl_2$, 1:3 (mole/mole) 50 mM phosphate, pH 7.0 |
| Concentration | pH 5.5 |
| Filtration | pH ≤ 3, 0.45 µm filter |
| Preparative RP-HPLC | Vydac® C-4 bonded phase silica gel, 2 propanol/acetic acid |
| Precipitation | Add one equivalent volume of 0.8 N NaOH into HPLC pool |
| Solubilization | solubilize HPLC precipitate in 0.1M $Na_2HPO_4$, 1% SDS |
| Sephacryl® S200 column | 50 mM acetate, pH 5.5, 0.1% SDS, 1 mM EDTA |
| Desalting–Sephadex G-25 column | pH is raised to 9–9.2; 0.1% sodium laurate as transfer component, 10 mM $Na_2HPO_4$ |
| Stabilization | pH of filtrate lowered to 3 with HCl (1–3 M); sodium laurate precipitates |
| Filtration | 0.22 µm filter |
| Formulation | 2.5% NSA at pH 3 to 3.2 added; incubation 5–15 minutes |
| Neutralization | pH is raised to 7.5 with NaOH |
| Pre-filtration | 0.45 µM |
| Sterile filtration | 0.22 µM |
| Lyophilization | |
| Final container product | |

FIG. 2

IFN-β PROCESS

| | |
|---|---|
| Fermentation | |
| Cell concentration | |
| Cell wall and membrane disruption | homogenization |
| Diafiltration | 5 mM EDTA |
| Redisruption | 2 mM EDTA; 1% octanol (v/v); homogenization |
| Sucrose suspension | 15-23% sucrose (w/w) |
| Centrifugation | 10,000-15,000 xg |
| Paste solubilization | 2% SDS, phosphate buffered saline |
| Reduction | 10 mM DTT; 2% SDS; 2 mM EDTA; pH 9; heat to 50°C for 10 min. under nitrogen; cool to about 25°C; adjust pH to 7.4 with glacial acetic acid |
| Organic Extraction | 2-butanol/suspension (v/v) |
| Acid precipitation | pH 6.2; 2 mM DTT; 0.1% SDS |
| Centrifugation | 10,000-15,000 xg |
| Acid precipitate solubilization | 5% SDS; 5 mM EDTA; 50 mM phosphate buffer |
| Reduction | 20 mM DTT; pH 8.5; heat to 50 for 10 min. under nitrogen; cool to about 25°C |
| Sephacryl® S200 column | 50 mM acetate; pH 5.5; 1% SDS; 1 mM EDTA |
| Oxidation | Iodosobenzoic acid (IBA) equimolar; protein:IBA; 0.1% SDS; 2 mM sodium pyrophosphate; pH 9; 1 mM EDTA |
| Concentration | pH 5.5 |
| Sephacryl® S200 column | 50 mM acetate; pH 5.5; 0.1% SDS; 1 mM EDTA |

FIG. 3A

| | |
|---|---|
| Concentration | |
| Sephadex® G-75 column | 50 mM acetate; pH 5.5; 0.1% SDS; 1 mM EDTA |
| Desalting—Sephadex® G-25 column | pH is raised to 9-9.2; 0.1% sodium laurate as transfer component in 10 mM disodium phosphate |
| Stabilization | pH of eluate is lowered to 3 with HCl (1-3 M); sodium laurate precipitates |
| Filtration | 0.22 μM filter |
| Formulation | 2.2% PPF adjusted to pH 3 added to desalted pool; incubated for 5 to 15 minutes |
| Neutralization | pH raised to 7.5 with NaOH |
| Pre-filtration | 0.45 μM |
| Sterile filtration | 0.22 μM |
| Lyophilization | |
| Final container product | |

FIG. 3B

FORMULATION PROCESSES FOR LIPOPHILIC PROTEINS

This is a division of the application Ser. No. 08/266,832, filed Jun. 28, 1994 which is a continuation of Ser. No. 07/865,411, filed May 7, 1992, now abandoned, which is a continuation Ser. No. 06/923,425, filed Oct. 27, 1986, now abandoned, which is a continuation-in-part of Ser. No. 06/775,751, filed Sep. 13, 1985 (U.S. Pat. No. 4,992,271) which is a continuation-in-part of Ser. No. 06/752,403, filed Jul. 5, 1985, now abandoned, which is a continuation-in-part of Ser. No. 06/592,077, filed Mar. 22, 1984, now abandoned, which is a divisional of Ser. No. 06/495,896, filed May 18, 1983 (U.S. Pat. No. 4,462,940) which is a continuation-in-part of Ser. No. 06/422,421, filed Sep. 23, 1982, now abandoned.

BACKGROUND OF THE INVENTION

This invention is in the general field of biochemical engineering. More specifically, the subject invention relates to the preparation of biologically active recombinant lipophilic proteins such as human interferons and interleukin-2. Still more specifically, the subject invention relates to an improved process for the production and recovery of lipophilic proteins from genetically transformed host organisms, lipophilic protein preparations relatively high purity, and therapeutically acceptable formulations thereof.

Interleukin-2 (IL-2) is a lymphokine which is produced by normal peripheral blood lymphocytes and induces proliferation of antigen or mitogen stimulated T cells after exposure to plant lectins, antigens, or other stimuli. IL-2 was first described by Morgan, D. A., et al., Science (1976) 198: 1007–1008 and was then designated T cell growth factor because of its ability to induce proliferation of stimulated T lymphocytes. Now renamed as interleukin-2, IL-2 later has been found also to modulate a variety of functions of immune system cells in vitro and in vivo. IL-2 is one of several lymphocyte-produced messenger-regulatory molecules which mediate immunocyte interactions and functions.

Human IL-2 has been obtained from genetically engineered E. coli as an unglycosylated protein with biological activities equivalent to those of native, glycosylated IL-2. [Devos et al., Nuc. Acids. Res., 11: 4307–4323 (1983); Rosenberg et al., Science, 223: 1412–1415 (1984); Wang et al., Science, 224: 1431–1433 (1984); and Doyle et al., J. Biol. Resp. Modifiers, 4: 96–109 (1985)] Rosenberg and his co-workers have shown that systemic administration of recombinant IL-2 in high doses causes regression of established metastases in mice [Rosenberg et al., J. Exp. Med., 161: 1169–1188 (1985)]; and, in conjunction with lymphokine-activated killer cells, in humans [Rosenberg et al., New Eng. J. Med., 313: 1485–1492 (1985)].

IL-2 was initially made by cultivating human peripheral blood lymphocytes (PBL) or other IL-2-producing cell lines. See, for example, U.S. Pat. No. 4,401,756. Recombinant DNA technology has provided an alternative to PBLs and cell lines for producing IL-2. Taniguchi, T., et al., Nature (1983) 302: 305–310 and Devos, R., Nucleic Acids Research (1983) 11: 4307–4323 have reported cloning the human IL-2 gene and expressing it in microorganisms.

Naturally occurring interferons (IFNs) are species-specific proteins, often glycoproteins, produced by various cells upon induction with viruses, double stranded RNAs, other polynucleotides, antigens and mitogens. Interferons exhibit multiple biological activities such as antiviral, antiproliferative, immunomodulatory and anticellular functions. At least three distinct types of human interferons have been identified and characterized in terms of their anti-viral, anti-growth and activation of natural killer cell (NK) activities. They are produced by leukocytes, lymphocytes, fibroblasts and the immune system and are classified as α, β and γ interferons. These are reported to be different proteins coded for by distinct structural genes.

Native human β-interferon (β-HIFN) is generally produced by superinducing human fibroblast cultures with poly-IC (polyriboinosinic acid and polyribocytidylic acid) and isolating and purifying the β-HIFN thus produced by chromatographic and electrophoretic techniques. Proteins or polypeptides which exhibit native β-interferon like properties may also be produced using recombinant DNA technology by extracting poly-A-rich 12S messenger RNA from virally induced human cells, synthesizing double-stranded c-DNA using the m-RNA as a template, introducing the c-DNA into an appropriate cloning vector, transforming suitable microorganisms with the vector, harvesting the bacteria and extracting the β-HIFN therefrom. Nagola, S. et al., Nature, 284: 316 (1980); Goeddel, D. V. et al., Nature, 287: 411 (1980); Yelverton, E. et al., Nuc. Acid Res., 9: 731 (1981); Streuli, M. et al., Proc. Nat'l. Acad. Sci. (U.S.), 78: 2848 (1981); European Pat. Application Numbers 28033, published May 6, 1981; 321134, published Jul. 15, 1981; 34307 published Aug. 26, 1981; and Belgian Patent 837397, issued Jun. 1, 1981 describe various currently used methods for the production of β-interferon employing recombinant DNA techniques. The expressed proteins or polypeptides have been purified and tested and have been found to exhibit properties similar to those of native IFNs. Bacterially produced IFNs thus appear to have potential therapeutic use as antiviral and antitumor agents and the production of IFNs by such bacterial fermentations is expected to yield sufficiently large quantities of IFN at a relatively low cost for clinical testing.

Protein samples for use in clinical studies, however, must be of relatively high purity and substantially uncontaminated with toxic host cell constituents, cell debris and other extraneous chemicals introduced during the extraction and purification steps. There are several methods currently available for the preparation, recovery and purification of bacterially produced proteins.

U.S. Pat. No. 4,315,852 to Leibowitz et al. describes and claims a method for the acid extraction of leukocyte interferon from bacterial cells and neutralization of the extractant to obtain the interferon.

Derynck et al., Nature, 287: 193 (1980) teach lysing transformed E. coli cells using a solution containing 5M urea, 1% sodium dodecyl sulfate (SDS), and 1% 2-mercaptoethanol. The lysate, which was purified by chromatography, exhibited interferon activity.

Scandella and Kornberg, Biochemistry, 10: 4447 (1971) describe the preparation of a phospholipase from E. coli by solubilizing the cell membranes with SDS and precipitating the solubilized protein with 1-butanol.

U.S. Pat. No. 4,343,735, to Menge et al. teaches a process for the purification of interferon by partitioning it in an aqueous multi-phase system in the presence of ion exchangers which are soluble in the system and are derivatives of polyethers.

U.S. Pat. No. 4,343,736 to Uemura et al. discloses a method for recovering interferon by absorption on water-insolubilized heparin and then eluting the interferon with an aqueous solution of an inorganic salt and chondroitin sulfate.

U.S. Pat. No. 4,289,689 to Friesen et al. discloses how to recover and purify human native β-interferon by use of affinity chromatography and high pressure liquid chromatography.

U.S. Pat. No. 4,460,574 to Yabrov discloses a pharmaceutical composition comprising native human α- and β-interferons used for rectal or urogenital treatment of human interferon-sensitive diseases.

U.S. Pat. No. 4,364,863 to Leibowitz et al. describes a method of extracting fibroblast interferon from bacteria using a low pH followed by a high pH extraction procedure.

PCT WO 80/02229 to Benzon discloses purification of alpha (leukocyte) interferon, which is not a lipophilic protein.

EP 42,246 discloses that recombinant interferons may be dissolved in any pharmaceutically acceptable non-toxic carrier appropriate for the desired form of administration without further details.

U.S. Pat. No. 4,450,103 discloses solubilizing the protein in an aqueous medium with an appropriate solubilizing agent, extracting the protein from the aqueous medium with 2-butanol or 2-methyl-2-butanol, and precipitating the protein from the alcohol phase.

*Cancer Treatment Reports*, 62, 1900–1906 (1978) and EP 89,245 disclose that native beta-interferon may be formulated directly with human serum albumin in a pharmaceutically compatible aqueous-based medium at a pH of 7.2–7.8.

Copending U.S. Ser. No. 780,551, filed Sep. 26, 1985, entitled "Stable Formulation of Biologically Active Proteins for Parenteral Injection" describes a pharmaceutical composition suitable for parenteral injection into humans or animals containing IL-2 or IFN-β dissolved in a suitable carrier medium at pH 7.0 to 8.0 stabilized with sodium laurate. The formulation can be prepared by adding to either protein, after its recovery from a transformed organism, an effective amount of sodium laurate at a pH of 9 to 9.5 and then adjusting the pH of the formulation to between 7.0 and 8.0.

EP 158,487, published Oct. 15, 1985, discloses an interleukin-2 composition which comprises human serum albumin, a reducing compound or a combination thereof, and which is adjusted to a pH from 3 to 6 as a solution.

Alpha-interferons and native beta-interferon are not lipophilic proteins. Therefore, they can be stabilized and solubilized by adding a stabilizer such as human serum albumin directly to the formulation at physiological pH. In contrast, lipophilic proteins such as recombinant beta-interferon and interleukin-2 are not solubilized by addition of human serum albumin at pH 6.8–7.8.

A major problem with the existing methods of purification and recovery of lipophilic proteins is that the protein is not produced in a sufficiently pure form and in sufficiently large quantities for clinical and therapeutic purposes. The resulting protein preparations, especially those that are produced by recombinant DNA techniques, also have residual amounts of chemicals, such as SDS and other surfactants or precipitants used in the extraction and purification steps. It would be desirable, therefore, to have available a process for the recovery of a lipophilic protein in sufficiently large quantities and sufficiently pure form for clinical and therapeutic applications. Also, it would be desirable to have formulations substantially free of residual chemicals or which have very low levels of such residual chemicals.

Accordingly, it is an object of the present invention to provide a pharmaceutically acceptable sample of a lipophilic protein such as recombinant β-interferon or interleukin-2 which is of relatively high purity and in sufficiently large quantities for clinical and therapeutic applications.

Yet another object of the instant invention is to provide lipophilic proteins such as recombinant β-interferon or interleukin-2 preparations which are substantially free of SDS or contain very low levels of SDS without loss of the lipophilic protein's biological activity.

A further object of this invention is to provide recombinant β-interferon and interleukin-2 samples wherein the level of SDS is less than about 10 p.p.m.

U.S. Pat. No. 4,462,940 which is in the series of patents and applications of which this application is a continuation-in-part, describes an improved method for the production, recovery and purification of a lipophilic protein such as human recombinant β-interferon and interleukin-2 and comprises solubilizing the protein into an aqueous medium with a suitable solubilizing agent, extracting the solubilized protein with an aliphatic alcohol, precipitating the protein from the alcohol phase with an aqueous buffer, and diafiltering the protein at a pH of about 10.5 to 12.5, preferably at a pH of about 12, against water adjusted to a pH of about 10.5 to 12.5, preferably about 12, or against mixtures of water and aliphatic alcohols, preferably ethanol and glycerol adjusted to a pH of about 10.5 to 12.5, preferably about 12, substantially to remove SDS or to reduce its concentration. The protein sample is optionally purified by conventional methods such as chromatography prior to the diafiltration.

A preferred embodiment of the above method comprises recovering bacterially produced human β-interferon by disruption of the bacterial cells, solubilization of the interferon with a suitable solubilizing agent, extracting the solubilized interferon with an aliphatic alcohol of 2–6, preferably 4–6 carbon chain length, precipitating the interferon from the alcohol phase, further purifying the interferon by conventional methods, preferably gel filtration chromatography, and diafiltering the interferon fraction at a pH of about 10.5 to 12.5, preferably at a pH of about 11, against pure water or mixtures of water and aliphatic alcohols, preferably methanol, ethanol, propanol, butanol, glycerol and the like, also adjusted to a pH of about 10.5 to 12.5, preferably about 11. Said process results in human β-interferon formulations with levels of SDS less than about 10 p.p.M.

SUMMARY OF THE INVENTION

One aspect of the instant invention concerns a process alternative to the method described above and claimed in U.S. Pat. No. 4,462,940. Said process alternative avoids the high pH range (pH 10.5 to 12.5) required to remove certain solubilizing agents such as SDS during diafiltration or desalting.

Said process alternative of the instant invention comprises employing a transfer component during diafiltration or desalting. Said transfer component is a milder detergent or chaotrope which functions to replace stronger solubilizing agents such as SDS used in the extraction and purification of the recombinant lipophilic protein from the host strain. Such milder detergent/chaotropes used as transfer components allow for diafiltration or desalting of the lipophilic protein to occur at a lower pH range, for example, from a pH range of about 8.5 to about 10.0, preferably 9–9.5, and more preferably at pH 9.0–9.2. Examples of such detergent/chaotropes for use as transfer components include fatty acid salts having carbon chains of from 10 to 13 carbons, preferably 11 to 12, and most preferably 12 carbons. It is preferred that the fatty acid salt be a laurate salt and most preferred that such laurate salt be sodium laurate. It is further preferred that such transfer component be used in a low ionic strength elution buffer, for example, disodium phosphate or Tris-HCl at a concentration range of from about 5 mM to about 15 mM, preferably about 10 mM.

After diafiltration or desalting at a pH of about 8.5 to about 10 (preferably 9–9.5, more preferably 9–9.2), the pH of the diafiltrate or desalted pool can be adjusted with an appropriate acidic agent such as hydrochloric acid (1–3M) to approximately 2–4, preferably to a pH of 3–4, and most preferably about 3.5, at which pH the transfer component will precipitate from the solution and can be removed by filtration, centrifugation or other appropriate means known to those skilled in the art. Lipophilic proteins, such as, recombinant IL-2 and β-HIFN, are stable and soluble at this low pH range. Such a low pH solution containing the lipophilic protein does not require a stabilizer and, therefore, provides an alternative pharmaceutical composition for clinical use.

Said low pH formulation can either be maintained as a liquid, or a carbohydrate stabilizer such as dextrose or mannitol can be added thereto, and the formulation can be lyophilized and later optionally reconstituted.

Therefore, another aspect of the instant invention concerns a stable pharmaceutical composition comprising a therapeutically effective amount of a biologically active recombinant lipophilic protein dissolved in a non-toxic, inert, therapeutically compatible aqueous-based carrier medium at a pH of from about 2 to about 4, preferably 3 to 4 and most preferably at about pH 3.5.

Further, alternatively, a protein stabilizer without prior extreme alkaline treatment and preferably adjusted to the pH range of the lipophilic protein pool can be added to the low pH lipophilic protein solution resulting in a pharmaceutical composition having a pH of from about 2 to about 4, preferably 3–4, and more preferably about 3.5.

More preferably, the protein stabilizer without prior extreme alkaline treatment, and preferably adjusted to the pH range of the lipophilic protein pool, is added to the low pH lipophilic protein solution and incubated therewith at the low pH range for from about 5 to 45 minutes, preferably from 5 to 15 minutes, and then raised with an appropriate base, such as sodium hydroxide, to a pH of from about 6.8 to 7.8, preferably 7.2 to 7.6, most preferably about 7.5, for clinical administration. The formulation is filtered and/or centrifuged, preferably filtered, to remove the precipitated transfer component. It can be maintained as a liquid, or a polyol can be added thereto, preferably dextrose or mannitol, and it can be lyophilized and later reconstituted for clinical administration.

Said process alternative employing a transfer component during diafiltration or desalting at a pH range of from about 8.5 to about 10.0 (preferably 9 to 9.5, and more preferably 9 to 9.2) is a preferred route for recombinant HIFN-β.

An alternative formulation route for recombinant IL-2 concerns a process wherein the partially purified IL-2 is diafiltered or desalted at a pH range from about 8.5 to about 10.0, preferably from about 9 to about 9.5 and more preferably at pH 9–9.2 without employing a transfer component. The recombinant IL-2 can be formulated at said pH range with a protein stabilizer that in a continuous sequence up to addition was exposed to a pH range of from about 10.5 to about 12.5, preferably at a pH range from about 11 to about 12, and maintained at said pH range for from about 5 to about 45 minutes, preferably from about 10 to about 30 minutes, and more preferably from about 10 to 15 minutes, and then adjusted to a pH of from about 8.5 to 10.0, preferably 9 to 9.5, and most preferably at pH 9–9.2 immediately before addition to the purified IL-2 pool. The formulation can then be maintained at the pH range at which it was formulated as a liquid or, optionally, a polyol can be added and it can then be lyophilized. Alternatively, the protein stabilizer and IL-2 formulation can be incubated for a period of from about 0 to 60 minutes, preferably 5 to 45 minutes, more preferably 5 to 15 minutes, and then the pH of the solution can be lowered with an appropriate acidic agent to a pH closer to physiologic pH from about 6.8 to 7.8, preferably 7.2 to 7.6, most preferably about 7.5. Optionally, a carrier as a polyol can be added to the formulation, and it can be lyophilized. The lyophilized formulation can then be reconstituted for clinical administration at the clinician's option.

A further alternative preferred formulation route for recombinant IL-2 is a variant of the high pH formulation route described in great detail for recombinant HIFN-β in a parent application which issued as U.S. Pat. No. 4,462,940. (Said '940 patent is discussed above in the Background.) Chemical agents such as SDS used in the extraction and purification of IL-2 are removed by diafiltration or desalting at a pH range of from about 10.5 to about 12.5, preferably from about 11 to 12. A protein stabilizer adjusted to such pH range is added to the purified IL-2, and the mixture is incubated for from about zero to fifteen minutes. The pH of the pool is then lowered with an appropriate acidic agent to a pH range from about 6.8 to about 7.8, preferably from about 7.2 to about 7.6, most preferably to about 7.5. The formulation can then be maintained as a liquid at said pH range or optionally a carrier such as dextrose can be added thereto, and the formulation can be lyophilized. The formulation can then be reconstituted for clinical administration at the clinician's option.

Therefore, in another aspect, the therapeutic formulations of this invention are stable pharmaceutical compositions comprising a therapeutically effective amount of a biologically active recombinant lipophilic protein dissolved in a non-toxic, inert, therapeutically compatible aqueous-based carrier medium at a pH of 6.8 to 7.8 (preferably 7.2 to 7.6, and more preferably about 7.5) comprising a stabilizer for the protein.

The lipophilic protein, preferably recombinant β-HIFN or IL-2, is in a therapeutically effective amount in said stable pharmaceutical compositions. Preferably, the therapeutically effective amounts are in the range of 0.05 to 10 mg per ml of the carrier medium, more preferably from about 0.1 to about 5 mg of lipophilic protein per ml of the carrier medium.

Preferably, the protein in all such formulations is β-interferon or interleukin-2 and the stabilizer is human serum albumin (HSA), a mixture of human serum albumin and dextrose, or human plasma protein fraction (PPF).

In a further aspect of the present invention, the therapeutic protein preparation obtained from the diafiltration or desalting and stabilization steps may be lyophilized and reconstituted in an inert, non-toxic, physiologically compatible carrier medium for therapeutic and clinical applications.

DETAILED DESCRIPTION OF THE PREFERRED EMBODIMENTS

As used herein, the term "lipophilic protein" refers to a protein which is not soluble or not readily soluble in an aqueous medium under ambient conditions of room temperature and atmospheric pressure at a pH of between about 6.5 and 7.8. Examples of such proteins include human recombinant β-interferon, recombinant interleukin-2 and immunotoxins prepared by conjugating a cytotoxin moiety such as ricin A to an antibody against a pathologic condition such as breast cancer. The term "recombinant protein" refers to a protein which is produced by recombinant DNA techniques wherein generally DNA is inserted into a suitable expression plasmid which is inserted into a host organism not native to the DNA which is transformed to produce the heterologous protein. The host may be any organism foreign to the DNA such as, e.g., bacteria, yeast, viruses, mammals, etc. Preferably the host is microbial, and most preferably is bacterial.

As used herein, the term "β-HIFN" refers to human interferon or β-interferon-like polypeptides produced by recombinant DNA techniques and whose amino acid sequence is the same as or similar or substantially homologous to the unglycosylated and/or glycosylated native β-interferon.

As used herein the term "IL-2" refers to human interleukin-2 or interleukin-2-type polypeptides produced by recombinant DNA techniques and whose amino acid sequence is the same as or similar or substantially homologous to the unglycosylated and/or glycosylated native interleukin-2.

The precise chemical structure of the protein will depend on a number of factors. As ionizable amino and carboxyl groups are present in the molecule, a particular protein may be obtained as an acidic or basic salt, or in neutral form. All such preparations which retain their activity when placed in suitable environmental conditions are included in the definition of proteins herein. Further, the primary amino acid sequence of the protein may be augmented by derivatization using sugar moieties (glycosylation) or by other supplementary molecules such as lipids, phosphate, acetyl groups and the like, more commonly by conjugation with saccharides. Certain aspects of such augmentation are accomplished through post-translational processing systems of the producing host; other such modifications may be introduced in vitro. In any event, such modifications are included in the definition of protein herein so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Finally, modifications to the primary structure itself by deletion, addition, or alteration of the amino acids incorporated into the sequence during translation can be made without destroying the activity of the protein. For example, U.S. Pat. No. 4,588,585, herein incorporated by reference, discloses muteins (analogs) of IFN-β in which the cysteine at position 17, numbered in accordance with native IFN-β, is deleted or replaced by a neutral amino acid, such as, serine or threonine, preferably serine. U.S. Pat. No. 4,518,584 discloses muteins (analogs) of IL-2 in which the cysteine normally occurring at position 125 of the wild-type or native molecule has been replaced with a neutral amino acid, such as serine or alanine. The '584 patent, incorporated herein by reference, also discloses a preferred modification of the N-terminal IL-2 sequence wherein the alanine at position 1 is deleted. Co-pending, commonly owned U.S. Ser. No. 893,186, filed Aug. 5, 1986 discloses further muteins of IFN-β and IL-2 wherein a conservative amino acid of a biologically active protein such as IL-2 or IFN-β is substituted for each methionine residue susceptible to chloramine T or peroxide oxidation, wherein additional, non-susceptible methionine residues are not so substituted. A conservative amino acid alteration in this context is defined as one which does not adversely affect biological activity and involves neutral or non-polar amino acid substitutions or deletion of the methionine. In a preferred example of this embodiment the methionine at amino acid position 104 of IL-2 is replaced by an alanine residue.

Preferably the protein herein is β-HIFN or IL-2. Most preferably the protein is unglycosylated β-HIFN or IL-2 which is produced by a microorganism that has been transformed with a human IFN-β or IL-2 gene or a modification of the human IFN-β or IL-2 gene that encodes a protein having: (a) an amino acid sequence that is at least substantially identical to the amino acid sequence of native human IFN-β or IL-2 and (b) biological activity that is common to native human IFN-β or IL-2. Substantial identity of amino acid sequences means the sequences are identical or differ by one or more amino acid alterations (deletions, additions, substitutions) that do not cause an adverse functional dissimilarity between the synthetic protein and the native human IFN-β or IL-2. Examples of such proteins are the IFN-β or IL-2 proteins described in U.S. Pat. Nos. 4,518,584 and 4,588,585. Most preferably, the IFN-β is $ser_{17}$IFN-β wherein the cysteine residue at amino acid position 17 is replaced by a serine residue.

Preferred recombinant IL-2s include those wherein the cysteine residue at position 125 and/or the methionine residue at position 104 are replaced with a conservative amino acid; those wherein the N-terminal alanine residue of the native counterpart is eliminated; those wherein the first five amino acids are deleted; those wherein the initial alanine residue is eliminated and the cysteine at position 125 is replaced by a conservative amino acid; and those wherein the initial alanine residue is eliminated, and the cysteine at position 125 as well as the methionine at position 104 are replaced by conservative amino acids. More particularly, preferred recombinant IL-2 muteins in the formulations of this invention are those wherein the cysteine residue at amino acid position 125 of the native counterpart is replaced by a serine residue (designated IL-$2_{ser125}$) or alanine residue (designated IL-$2_{ala125}$); those wherein the N-terminal alanine residue of the native counterpart is eliminated; those wherein the initial alanine residue is eliminated and the cysteine at position 125 is replaced by serine (designated des-alanyl-IL-2$_{ser125}$); those wherein the methionine at position 104 is replaced by alanine (designated IL-2$_{ala104}$); and those wherein the initial alanine is eliminated, the methionine at position 104 is replaced with alanine and wherein the cysteine at postion 125 is replaced with serine (designated des-alanyl-IL-2$_{ala104, ser125}$).

Further examples of recombinant IL-2s which are substantially homologous to the unglycosylated and/or glycosylated native IL-2 include those described in European published patent applications 91539, 88195 and 109748, and bovine IL-2 as described by Cerretti et al., *PNAS*, 83: 3223–3227 (1986).

As used herein, the term "physiological pH" refers to a pH which is pharmaceutically acceptable to mammals, i.e., a pH of about 7.2–7.6.

As used herein, the term "human serum albumin" is intended to encompass within its meaning normal serum albumin (NSA), which is clinical grade human serum albumin.

As used herein, the term "stabilizer" as applying to the lipophilic protein refers to non-toxic, non-therapeutic, non-immunogenic compositions which act not only to stabilize the diafiltered or desalted protein against denaturation and loss of biological activity, but also to solubilize the lipophilic protein in an aqueous medium so that the pharmaceutical formulation constitutes an aqueous solution of diafiltered or desalted protein at pH 6.8–7.8 from which the protein will not precipitate. Such stabilizers are not known in the art for their solubilizing function. Examples of such stabilizers include, but are not limited to, proteins or carbohydrates preferably chosen from the proteins human serum albumin (HSA), and human plasma protein fraction (PPF), and the carbohydrates (polyols) mannitol, galactitol, inositol, xylitol, sorbitol, glycerol, dextrose, lactose or a mixture thereof.

The type of stabilizer employed and the concentration thereof will depend mainly on the pH method and formulation employed and on the protein. For example, HSA, or a mixture of HSA and dextrose is preferred for high pH formulations and formulations treated at low pH using an analog of IL-2. However, for low pH formulations using IFN-β$_{ser17}$, PPF is preferred. PPF is commercially available and is composed of at least 83% albumin and no more than 17% globulins (α and β); no more than 1% of the proteins are gamma-globulins. The α- and β-globulins in blood plasma serve several functions, one of which is to hold in stable aqueous solution relatively insoluble blood components, including cholesterol, fat-soluble vitamins, and hormones. Carbohydrate stabilizers alone can only be used in formulations maintained/lyophilized at pH 2–4.

The final concentration of stabilizer generally may range from 0.1–10% (w/v) depending mainly on the protein and type of stabilizer and the pH employed, with higher ranges preferred for low pH. A range of 0.5 to 10% (w/v) is typical for HSA with β-HIFN; 0.1 to 5% (w/v) is typical for PPF with β-HIFN and IL-2; and 0.5–10% (w/v) is typical for HSA with IL-2.

Many of the methods used for the recovery of lipophilic recombinant proteins, such as bacterially produced β-HIFN, utilize SDS or similar surfactants for the solubilization and isolation of the protein from cellular material and subsequent acid precipitation to obtain the protein. By further purification techniques carried out at or near neutral pH, the SDS levels in the final protein preparations are reduced to about 0.1%. Further removal of SDS by diafiltration techniques in the 4–8 pH range results in almost complete loss of β-HIFN activity due to aggregation and precipitation of the protein. The biological activity of β-HIFN lost during diafiltration or desalting may be regained by the addition of SDS.

For a free or unbound solute, the removal rate during diafiltration from a well mixed vessel follows first order kinetics. Since unbound SDS below its critical micelle concentration is a molecule small enough to pass unhindered through a 10,000 dalton cut-off membrane, its removal rate would be expected to follow first order kinetics, and if that were the case, SDS at an initial concentration of about 1000 μg/ml should be reduced to less than 1 μg/ml after about seven volume replacements. It was found, however, that SDS removal from β-HIFN did not fit this theoretical model, indicating that there were protein-SDS interactions which significantly affected the kinetics of SDS removal, and that SDS removal from this bound state in the 4–8 pH range promoted protein-protein interactions resulting in aggregation or precipitation of the protein. Higher or lower pH ranges for SDS removal would not be expected to be desirable, as at higher or lower pH, some proteins are known to be denatured. However, according to the present invention, following the removal of SDS by diafiltration at low ionic strength or by desalting, increasing or decreasing the pH by the addition of base or acid, respectively, solubilizes the protein and essentially restores its biological activity in the formulation.

Thus, the present invention solves the problem of lipophilic protein aggregation and precipitation and loss of protein activity with the removal of SDS. One solution to the problem, as described and claimed in U.S. Pat. No. 4,462,940 (see above), involves initially adjusting the pH to about 10.5 to 12.5 and diafiltering against distilled water or aqueous mixtures of alcohols, using a 10,000 molecular weight cut-off ultrafiltration membrane after optionally reducing a partially purified sample of the protein with dithiothreitol (DTT) or mercaptoethanol or glutathione or cysteine at about 60° C. and a pH of about 8.5 to prevent aggregation of the protein. Exemplary alcohols include ethanol, butanols, glycerol, mannitol, sorbitol, dextrose and the like.

U.S. Pat. No. 4,462,940 to Hanisch et al. discloses a process wherein β-HIFN is formulated by the high pH route shown for IL-2 on the right-hand side of FIG. 1. When 10% HSA at pH 6.8 to 7.8 is added to recombinant β-HIFN diafiltered at about pH 11 to about pH 12 and at the time of addition at about pH 11.5, the β-IFN precipitates from solution when the pH of the mixture is lowered to physiological pH. Only when the pH of both the HSA and β-HIFN are adjusted to the high pH range, preferably about pH 11.5 before mixing, does the β-HIFN remain in solution when the pH of the formulation is lowered to physiologic pH. Therefore, for this formulation route, a specific pH adjustment procedure is required.

Experiments were performed wherein IFN-$\beta_{ser17}$ was purified up to the point of the desalting or diafiltration step according to the procedures outlined below, and then mixed directly with HSA at a pH range that approximated physiologic pH. The β-interferon precipitated from the mixture. Specifically, the Sephadex® G-75 column containing approximately 0.1% SDS and 1.88 mg/ml of the recombinant β-IFN protein at pH 5.5, was mixed in test tubes with 0.4, 0.8 or 1.2 ml of HSA. The final pH range of each formulation was in the range of 6.8–7.2, and in each case the β-interferon precipitated from the formulation. The same results would be expected to occur if the final pH were increased up to 7.8. Therefore, it was concluded that the lipophilic protein cannot merely be mixed with HSA as a stabilizer at a pH in the range of 6.8–7.8.

Another solution which avoids the high alkaline pH range of 10.5 to 12.5 of the above-described method is to employ a milder detergent/chaotrope as a transfer component during diafiltration to remove stronger solubilizing agents, such as SDS, at a lower pH range of from 8.5 to 10.0, preferably 9 to 9.5, and more preferably 9 to 9.2. Preferably, the transfer component is a fatty acid salt having a carbon chain of from 10 to 13 carbons, preferably 11–12 carbons, most preferably 12 carbons. It is further preferred that said fatty acid salt is a laurate salt, most preferably sodium laurate. The concentration range of said transfer component in a low ionic strength elution buffer is from about 0.05 to about 2%, preferably from about 0.2% to about 1%.

In addition to such fatty acid salts, a number of other detergent/chaotropes can be used as, for example, urea (5–7 molar, preferably 6M) or more preferably guanidine hydrochloride (5–7 molar, preferably 6M).

Another solution to the problem involves initially adjusting the pH of the purified protein pool to about 2 to about 4, adding the stabilizer previously adjusted to a pH of 2 to 4, optionally incubating the mixture and raising its pH to 6.8 to 7.8. Incubation time depends mainly on the type of protein, type of stabilizer, exact pH, and concentrations of protein and stabilizer, and typically ranges from 0–100 minutes, preferably 10–100 minutes, more preferably 15–60 minutes, and most preferably 15–45 minutes.

In another but less preferred, solution to the problem, where the pH is low, the stabilizer and protein pool are mixed together and the pH of the mixture is adjusted to 2 to 4, and the pH is raised, gradually or at once, to 6.8–7.8.

The subject invention therefore includes a process for the recovery of lipophilic recombinant proteins of relatively high purity which contain low levels of SDS and which can be reconstituted into therapeutically acceptable formulations in an appropriate carrier medium, and lipophilic protein compositions, more preferably β-HIFN or IL-2 compositions, wherein SDS levels are at less than 10 p.p.m., usually in the range of 2–6 p.p.m. Preferably a high pH range can be avoided by employing a transfer component during diafiltration or desalting of said proteins. Where a transfer component is employed, the pH need not exceed 10, preferably 9.5, and most preferably 9.2, during purification.

The preferred diafiltration or desalting method for recombinant HIFN-β is said method employing a transfer component. However, recombinant IL-2 can be diafiltered or desalted at a pH range of 8.5 to 10, preferably 9 to 9.5, or more preferably 9 to 9.2 without a transfer component.

For purposes of practicing the present invention, bacteria are the preferred microorganism hosts, with *E. coli* being the most preferred.

Preferred embodiments of the processes of the instant invention are summarized below.

Figure 3A:
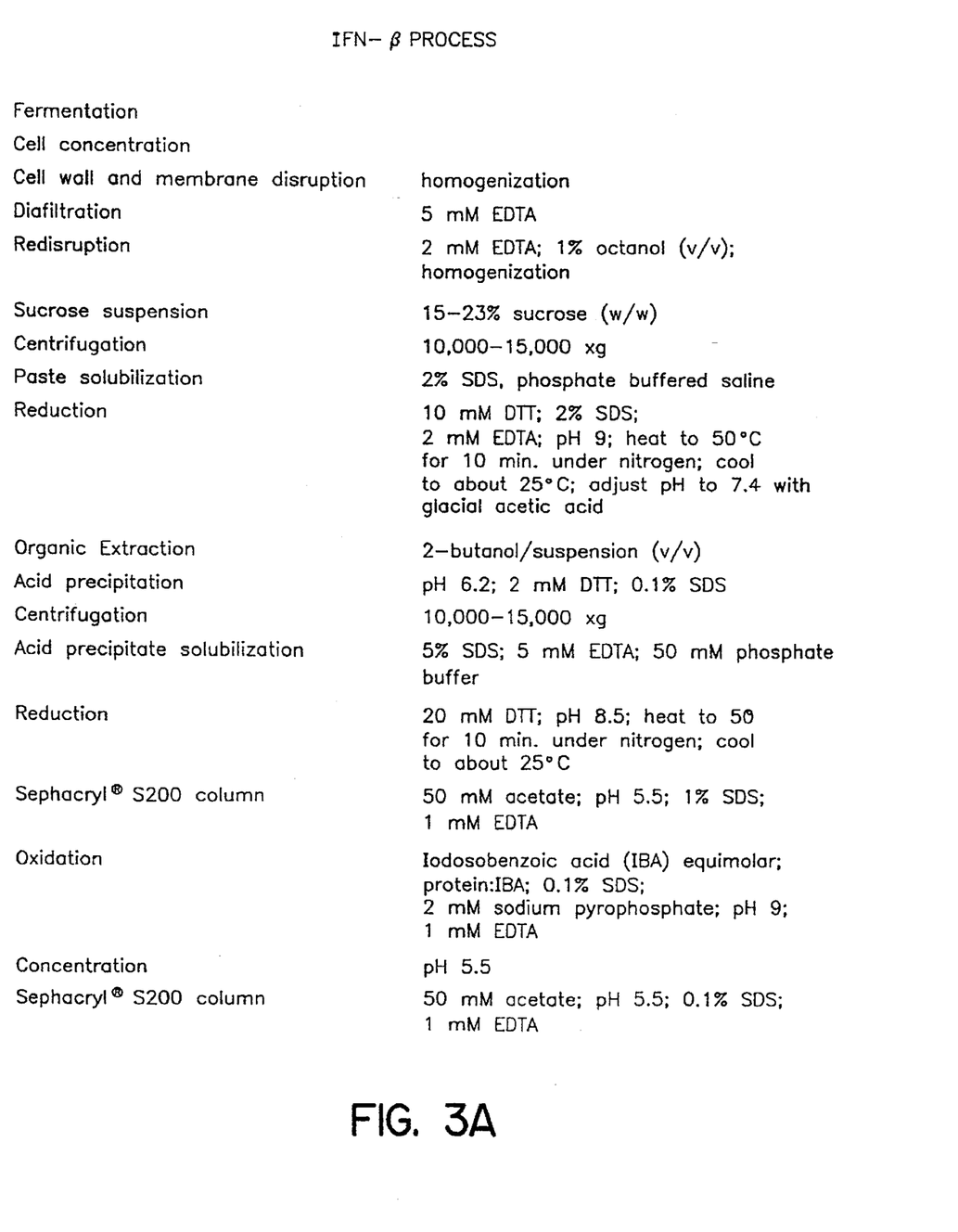
Figure 3B:
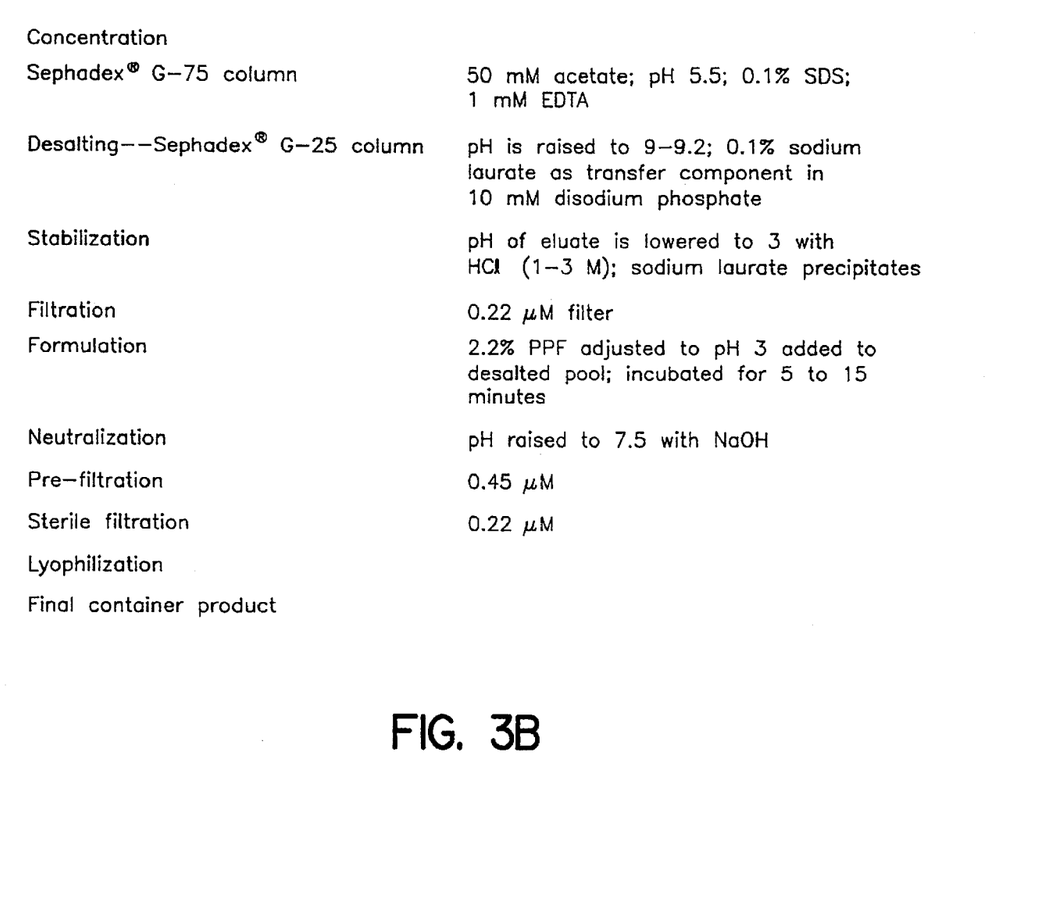

FIGS. 3A–B illustrate the details of the individual process steps of a preferred embodiment of the present invention including the culture of the transformed microorganisms in an appropriate fermentation medium through the final step where the purified β-HIFN is stabilized and may then be lyophilized and reconstituted into therapeutic formulations. The individual process steps include:

(a) growing the transformed bacterial hosts in an appropriate fermentation medium;

(b) concentrating the bacteria in the fermentation medium by cross-flow filtration, centrifugation or other conventional methods;

(c) disrupting the cell wall and cell membrane of the bacteria;

(d) removing greater than 99% by weight of the salts from said disruptate by diafiltration or centrifugation;

(e) redisrupting the desalted disruptate;

(f) adding a material to the disruptate to increase the density or viscosity of the liquid within the disruptate;

(g) separating the refractile material from the cellular debris by high-speed centrifugation;

(h) solubilizing the refractile material in an aqueous buffer under reducing conditions;

(i) organically extracting the solubilized refractile material, preferably with 2-butanol or 2-methyl-2-butanol;

(j) isolating said refractile material from the extractant, preferably by employing an acid precipitation step followed by centrifugation;

(k) solubilizing the resulting β-HIFN particle pellet with distilled water or with an aqueous solution of SDS at a β-HIFN to SDS ratio of about 1: 3;

(l) adjusting the pH of the solution to about 8.5 and reducing the solubilized β-HIFN with dithiothreitol;

(m) purifying the reduced β-HIFN by chromatography;

(n) collecting the eluted fraction of the purified β-HIFN;

(o) further purifying the β-HIFN by gel chromatography and collecting the eluate containing the purified β-HIFN;

(p) desalting the purified β-HIFN eluate in a desalting column at pH 9.0 to 9.2 with a low ionic strength elution buffer containing from about 0.1% to about 1% sodium laurate;

(q) adjusting the pH of the desalted pool to about 3 to 4 with an appropriate acidic agent at which point the sodium laurate precipitates;

(r) filtering the desalted β-HIFN pool to remove the precipitate;

(s) adding a protein stabilizer of this invention that has been adjusted to a pH range of from about 3 to 4 and incubating the mixture from about 15 to about 45 minutes;

(t) raising the pH of the solution with an appropriate basic agent to physiological pH;

(u) lyophilizing the β-HIFN sample; and (v) reconstituting the lyophilized β-HIFN sample, if desired.

The desalting step is preferably accomplished by G25 chromatography.

Alternatively, the desalting step (p) above can be replaced with a diafiltration step. Preferred elution buffers of low ionic strength containing the transfer component are 10 mM disodium phosphate or 10 mM Tris-HCl.

Optionally, after the pH of the desalted or diafiltered pool has been lowered to a pH range of about 2 to 4, preferably 3 to 4, and more preferably about 3.5, and the precipitated sodium laurate has been removed by filtration, centrifugation or by other appropriate means known to those skilled in the art, a stabilizer need not be added. The β-HIFN formulation will remain stable and soluble in a pH range of from about 2 to about 4, preferably 3 to 4, and most preferably at about pH 3.5. The pool can be maintained as a liquid with or without a carbohydrate stabilizer; or a carbohydrate stabilizer, preferably dextrose, can be added and the solution can be lyophilized. The lyophilized formulation can then be reconstituted for clinical administration.

Further, another alternative involves adding the protein stabilizer adjusted to the low pH range and eliminating the step of adjusting the pH to physiological pH. Such an alternative results in a low pH formulation which can be maintained as a liquid or, optionally, a carbohydrate stabilizer can be added, and it can be lyophilized. The lyophilized mixture can be reconstituted for clinical administration.

A preferred protein stabilizer for β-HIFN in step (s) would be a 0.1 to 5%, by weight, solution of plasma protein fraction (PPF).

Further, alternatively, the protein stabilizer can be added directly to the desalted or diafiltered β-HIFN pool before the pH thereof is lowered to a pH range of about 2 to 4, preferably 3 to 4, and more preferably about 3.5. When the pH of the mixture is lowered, the sodium laurate transfer component precipitates and can be removed by filtration, centrifugation or other appropriate means. The mixture is incubated for about 15 to 45 minutes. The formulation can then be maintained at said pH range as a liquid or can be lyophilized at said low pH range. Optionally, it can then be neutralized with an appropriate basic agent, and can be maintained as a liquid or lyophilized at neutral pH.

Figure 2:
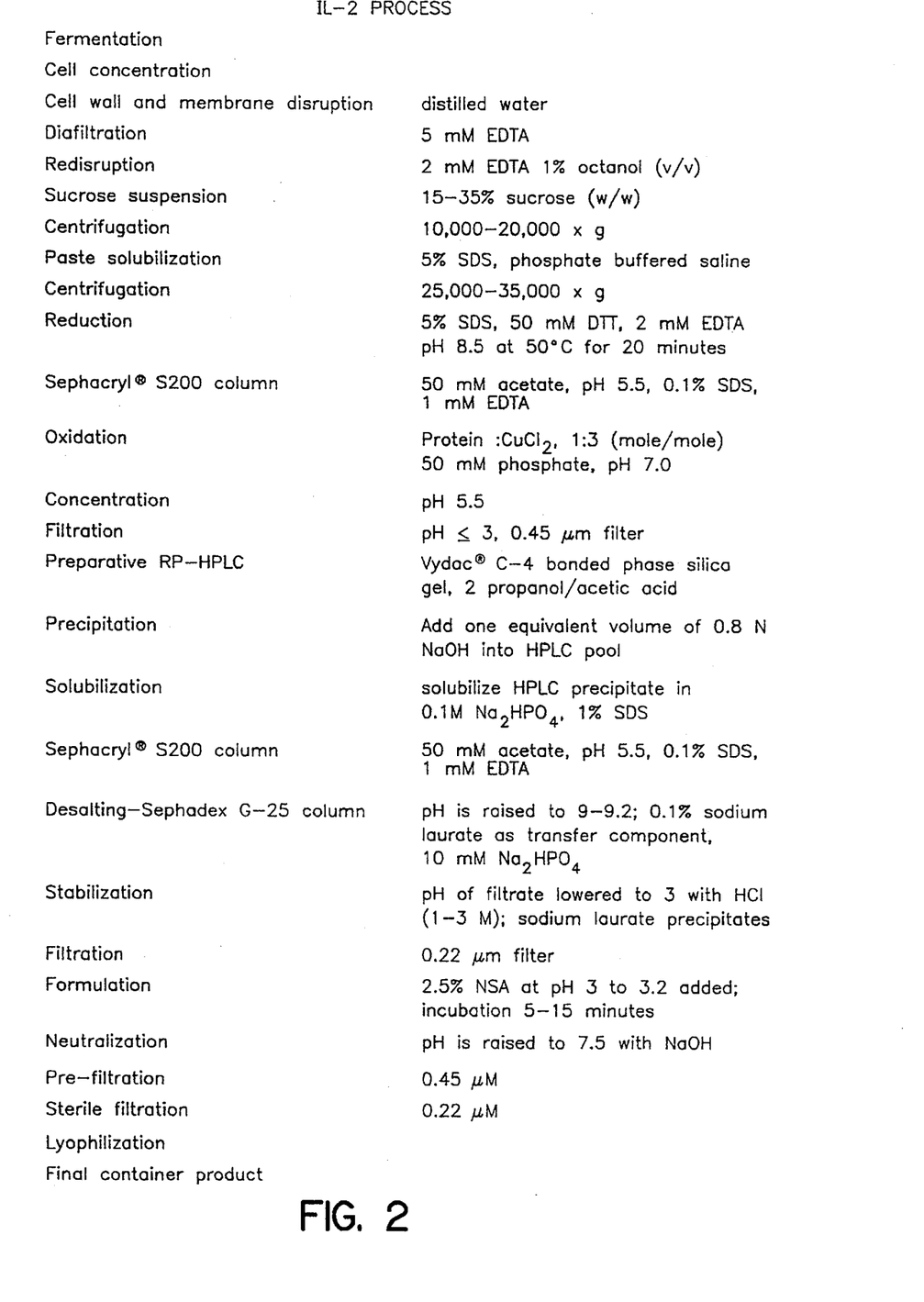
FIGS. 2 and 3A–B are flow charts sequentially illustrating preferred embodiments of the process steps of the present invention wherein recombinant IL-2 and recombinant HIFN-β, respectively, are recovered from refractile bodies, purified by a process wherein the last step of purification is a desalting step employing sodium laurate as a transfer component. In both embodiments, the formulation with the protein stabilizer is performed at a low pH.

Analogous processes as described above for β-HIFN can be used to extract, purify and stabilize/formulate recombinant IL-2 according to this invention. FIG. 2 outlines a preferred embodiment of the process steps of the present invention from culture of the transformed microorganism in an appropriate fermentation medium through the final step wherein the purified IL-2 is stabilized and may then be lyophilized and reconstituted, if desired, into therapeutic formulations. The particular process differences up to the point of desalting can be seen by comparing FIGS. 2 and 3A–B.

As with the β-HIFN formulation processes, recombinant IL-2 can be diafiltered or desalted at a pH range from about 8.5 to about 10, preferably 9 to 9.5, and more preferably at 9 to 9.2, wherein an elution buffer containing a transfer component, preferably sodium laurate is employed. Analogously, the pH of the diafiltrate or desalted pool is preferably lowered to a pH range of from about 2 to about 4, preferably 3 to 4, and most preferably 3.5, at which point the protein stabilizer, preferably human serum albumin (HSA) or normal serum albumin (NSA), that has been adjusted to the same pH range is added. Incubation, preferably from 15 to 45 minutes, follows before preferable neutralization and optional lyophilization are performed.

The other process alternatives described for β-HIFN apply to recombinant IL-2 formulation preparations. That is, for example, wherein the protein stabilizer is added prior to reducing the pH and precipitating the transfer component, preferably sodium laurate, and then the pH of the mixture is lowered to a pH range of about 2 to about 4, preferably 3 to 4, and more preferably, about pH 3.5. Further, the low pH formulation of IL-2 need not contain a protein stabilizer and can be maintained as a liquid with or without a carbohydrate stabilizer, or a carbohydrate stabilizer can be added thereto and it can be lyophilized.

A further preferred process of stabilizing and formulating recombinant IL-2 with the stabilizers of the present invention involves a process of diafiltering or desalting partially purified IL-2 at a pH range of about 8.5 to about 10, preferably at a pH of about 9 to 9.5, and more preferably at a pH of about 9 to about 9.2, without employing a transfer component. (See, for example, the middle route of FIG. 1.) The diafiltered or desalted IL-2 pool is then formulated at said pH range with a protein stabilizer that was exposed to a pH range of from about 10.5 to about 12.5, preferably from about 11 to about 12, for a period of from about 5 to about 45 minutes, preferably from 10 to 15 minutes, and then the pH of the stabilizer is lowered with an appropriate acidic acid to the pH range of the IL-2 pool just before addition. Preferably, the pH of the formulation can be maintained at said pH range of from about 8.5 to about 10, preferably from about 9 to about 9.5, and more preferably 9 to 9.2, or the pH thereof can be lowered to a pH closer to physiological pH from about 6.8 to 7.8, preferably 7.2 to 7.6, and most preferably about 7.5. The formulation can be maintained as a liquid or can be lyophilized and later reconstituted for clinical administration.

A further preferred formulation route for recombinant IL-2 is a high pH formulation process. In such a preferred process, the extracted and partially purified IL-2 is diafiltered or desalted at a pH range of from about 10.5 to about 12.5, preferably at a pH range of from about 11 to about 12. The protein stabilizer adjusted to a pH range of about 10.5 to about 12.5, preferably from about 11 to about 12, and more preferably about pH 12, is then added to the diafiltered or desalted IL-2 pool. The mixture is then incubated for a period of from about zero to about 45 minutes, preferably from about zero to 15 minutes, before the pH of the solution is lowered to physiologic pH with an appropriate acidic agent such as HCl (1–3M). The formulation can then be maintained at physiologic pH as a liquid or can be lyophilized. The lyophilized formulation can later be reconstituted for clinical administration.

A comparison of FIGS. 2 and 3A–B indicates some of the alternative optional steps in the extraction and purification processes for lipophilic proteins in general as well as the more detailed differences for the specified IL-2 and β-HIFN processes.

Notably, FIG. 2 exemplifies the abbreviated front-end for isolating refractile bodies containing a recombinant lipophilic protein whereas FIGS. 3A–B illustrate the expanded front-end process of isolating and recovering refractile bodies and refractile material containing a recombinant protein. In the abbreviated front-end process to recover refractile bodies, the refractile bodies are separated from the cellular debris by high-speed centrifugation. Whereas in the expanded front-end process, the "particle pellet" obtained from the last centrifugation step of the abbreviated front-end process is solubilized, reduced and then extracted from the aqueous medium with an organic extractant, preferably 2-butanol or 2-methyl-2-butanol. The extractant phase is then precipitated with an acid and centrifuged to produce a "final pellet" or "final paste" which is then further purified as exemplified in FIGS. 3A–B. Copending, commonly owned U.S. application Ser. No. 843,997 filed Mar. 25, 1986 (Dorin et al.) entitled "Process for Recovering Refractile Bodies Containing Heterologous Proteins from Microbial Hosts" details the procedures for extracting and purifying recombinant proteins, such as IL-2 and β-HIFN, which are deposited within the microbial host in refractile bodies. Said application is herein incorporated by reference. A synopsis of said procedures follows.

The transformed microorganisms are grown in a suitable growth medium, typically to an optical density (OD) of at least about 30 at 680 nm, and preferably between about 20 and 40 at 680 nm. The composition of the growth medium will depend upon the particular microorganism involved. The medium is an aqueous medium containing compounds that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical*

*Biology*, Lange Medical Publications, 14th Ed pp. 80–85 (1980).) In expression vectors involving the trp promoter, the tryptophan concentration in the medium is carefully controlled to become limiting at the time the recombinant β-HIFN or IL-2 expression is desired. Growth media for *E. coli* are well known in the art.

After the cells are harvested from the culture, they may be concentrated, if necessary, to about 20 to 150 mg/ml, preferably 80 to 100 mg/ml (OD 40 to 300, preferably 160 to 200 at 680 nm) by cross-flow filtration, centrifugation, or other conventional methods. Preferably a compound which is non-toxic to humans, such as 1-octanol, in an amount of about 1% by weight of total components, is added to the fermenter before or during cell concentration to ensure that no viable recombinant organisms remain before containment is broken.

Following concentration of the harvested culture, the cell walls and membranes of the microorganisms are disrupted. Conventional cell disruption techniques such as homogenization, sonication, or pressure cycling may be used in this step of the process. Preferred methods are sonication or homogenization with a homogenizer. The end point of the disruption step can be determined by monitoring the optical density with the absorbance at 260 nm of the suspension typically increasing with cell lysis. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining the heterologous protein as an insoluble complex in the cellular debris.

After the cells have been disrupted, deionized water is preferably added to the disruptate and greater than 99% by weight of the salts are removed therefrom. The removal of these salts to reduce the ionic strength of the disruptate may be accomplished by diafiltration using deionized water to flush out the ions or by centrifuging to pellet the cellular debris and refractile bodies followed by resuspension in deionized water.

After the salts are essentially removed, optionally a compound such as 1-octanol may be added to the desalted disruptate, if not added earlier, to ensure that no viable recombinant organisms remain. The desalted disruptate is again disrupted as described above for the initial disruption.

After redisruption, density or viscosity is increased and/or a gradient is created during centrifugation in the liquid within the disruptate by adding a material to the disruptate. One means to accomplish this goal is to add a material, such as sugar or mixtures of sugars, or a two-phase system such as a glycerol/sugar mixture, which increases the density of the liquid to about 1.1 to 1.3 g/ml, preferably 1.13 to 1.17 g/ml.

Also, the viscosity of the liquid phase may be increased to from 5 to 10 centipoise by any suitable means such as by adding a viscous compound such as sucrose or glycerol thereto.

In the final step of the abbreviated "front-end" process to recover the refractile bodies, the refractile bodies containing the desired protein are separated from the cellular debris by high-speed centrifugation. By "high-speed centrifugation" is meant spinning the suspension in a centrifuge at about 10,000 to 40,000 times gravity, preferably about 10,000–20,000 or 10,000–15,000 xg, for a suitable time period depending on the volume, generally about 10 minutes to seventy-two hours. The pellet resulting from this centrifugation is called the "particle pellet" or "particle paste."

In an alternative, expanded "front-end" process to recover the refractile bodies, the particle pellet obtained from the last centrifugation step of the abbreviated front-end process, is solubilized, reduced and then extracted from the aqueous medium with 2-butanol. The extractant phase is then precipitated with an acid and centrifuged to produce a "final pellet" or "final paste" which is then further purified as indicated.

The alternative, expanded front-end process is distinguished from the abbreviated front-end process in that it comprises several additional steps as follows: solubilizating the refractile bodies under reducing conditions; organically extracting the solubilized refractile material; and isolating said refractile material from the extractant. Essentially, the enhanced purity of the final pellet as opposed to the particle pellet lessens the purifying burden of downstream processing. There is an interdependence between the choice of the front-end process and later process purification steps to achieve the desired purity level for the final product. Once the choice of the particular front-end recovery of the refractile bodies has been made, one skilled in the art can pick and choose the alternative purifying steps outlined below to achieve the desired purity level of the final product.

For solubilizing the particle pellet in the expanded front-end, the following solubilizing agents can be used: sodium dodecyl sulfate (SDS), sodium laurate, urea, sodium dodecyl sulfonate, sodium dioctylsulfosuccinate, sodium decyl sulfate, sodium tetradecyl sulfate, sodium tridecyl sulfonate, sodium dodecyl N-sarcosinate, guanidine hydrochloride and sodium tetradecyl N-sarcosinate. Preferred solubilizing agents are SDS, guanidine hydrochloride or sodium laurate. Sodium laurate is most preferred when it is desired to reduce the level of SDS in the final container product.

The solubilizing agent is in an aqueous buffer, preferably phosphate buffered saline. The preferred percentage of the solubilizing agent is in the range of 1% to 5% (w/v). (Percentages herein reflect weight to volume ratios.) The most preferred solubilizing solution is phosphate buffered saline with 1–2% sodium laurate (20 mM $NAPO_4$) at pH 9–10. Sonication is preferably employed to promote solubilization when sodium laurate is the solubilizing agent of choice. Also, the use of a reducing agent aids solubilization.

Reducing agents that can be employed during the solubilization step include: mercaptoethanol, glutathione, cysteine and dithiothreitol (DTT). DTT is the most preferred reducing agent.

Optionally, said aqueous buffer can also contain a chelating agent in a concentration of from 3 to 7 mM. Most preferably, said chelating agent would be EDTA at a concentration of 5–6 mM, most preferably 5 mM.

The solubilization will typically be carried out at temperatures in the range of 20° C. to 25° C. with mixing to facilitate contact between the solid phase and the solubilizing medium.

A reduction step may be carried out wherein the pH, if necessary, may be adjusted to a range of about 8 to about 9. The suspension may be heated to 50°±5° C. for 5 to 15 minutes under nitrogen. The reaction mixture would then be cooled to approximately 25° C.

The solubilization is considered complete when the sample has sat 15 minutes or the solution turns translucent. Optionally at this point, the insoluble material may be separated by centrifugation or filtration after completing the solubilization.

After the protein is solubilized, the resulting suspension may optionally be centrifuged at 10,000–40,000 xg. The exact speed of centrifugation is not critical, as most of the insoluble material will come out, even at low speeds. The pellet is discarded and the supernatant containing the desired protein is retained and processed to recover the desired protein. Otherwise, after the solubilization or solubilization/ reduction step, the pH of the suspension can be adjusted to a pH of approximately 5 to 6, most preferably to 5.5 with glacial acetic acid, and then filtered.

If a reduction step was not carried out during the solubilization, the next step in the process would be a reduction of the solubilized refractile body protein. A preferred reducing agent is dithiothreitol (DTT). Reduction conditions may also include the addition of a chelating agent such as ethylenediaminetetraacetic acid (EDTA).

The next step in the process is to separate the protein in the supernatant from any host contaminants remaining after the centrifugation or filtration and optimally from the solubilizing agent. Gel filtration chromatography, reverse-phase high performance liquid chromatography (RP-HPLC), or a combination of gel filtration chromatography and RP-HPLC, can be used. The gel filtration chromatography is preferably carried out in two stages that remove both pyrogenic components and protein contaminants having molecular weights higher or lower than that of the protein. Gels that are capable of fractionating the solution to permit separation of the protein from these contaminants are commercially available. Sephacryl® S-200 is a preferred gel for removing the higher molecular weight components and Sephadex® G-25, G-75 or G-100 gels are preferred for removing the low molecular weight contaminants. The gel filtrations will typically be run in buffered solutions (pH 5.5 to 7.0) containing about 0.1% to 1.5% solubilizing agent and about 0.5 to 10 mM reducing agent. The column will be sized to permit suitable resolution of the desired components.

RP-HPLC is an alternative to gel filtration. Also, RP-HPLC is capable of removing molecules from the solution that have molecular weights close to the protein and cannot, therefore, be removed completely by gel filtration. In addition, contaminants such as bacterial endotoxin are also removed effectively by RP-HPLC. Therefore, RP-HPLC may also be used as a final purification step after gel filtration.

As indicated in FIGS. 2 and 3, both the recombinant Il-2 and β-IFN are respectively oxidized after undergoing gel filtration through a Sephacryl® S-200 column. U.S. Pat. No. 4,530,787 entitled "Controlled Oxidation of Microbially Produced Cysteine-Containing Proteins" (Shaked et al.) and U.S. Pat. No. 4,572,798 entitled "Method for Promoting Disulfide Bond Formation in Recombinant Proteins" (Koths et al.) disclose methods of oxidizing reduced cysteine-containing recombinant proteins, such as HIFN-β and IL-2, in a controlled, selective manner so that the recombinant proteins have essentially the same disulfide bridging and biological activity as their native counterparts. Both the '787 and '798 patents are herein incorporated by reference. The '787 patent employs o-iodosobenzoate as the oxidizing agent, and provides the preferred method of oxidizing recombinant HIFN-β. The method described in '798 patent employs an effective amount of an oxidation promoter containing a $Cu^{2+}$ cation, such as $CuCl_2$ or o-phenanthroline/$Cu^{2+}$ complex in the presence of air, and is the preferred method of oxidizing recombinant IL-2. The oxidized product is concentrated at a pH range of 5 to 7, preferably 5.5.

Recombinant IL-2 is then preferably filtered at a pH of less than 3 and purified by preparative RP-HPLC followed by a precipitation and solubilization step as outlined in FIG. 2. Preferably gel filtration on a Sephacryl® S200 column then follows. Preferably, it is the recombinant IL-2 which elutes from such an S200 column that is then stabilized and formulated according to the procedures of the present invention as disclosed above and further exemplified below and in outline form in the preferred embodiments of FIGS. 1 and 2.

In contrast, the oxidized and concentrated β-HIFN is preferably purified by gel filtration as indicated in FIG. 3. Preferably, it is purified by running it through a Sephacryl® S200 column, the eluate is then concentrated and run through a Sephadex® G-75 column. Most preferably, it is the recombinant β-HIFN that elutes from such a G-75 column that is stabilized and formulated according to the procedures of the present invention as disclosed above and further exemplified below and in FIG. 3.

However, recombinant IL-2 and β-HIFN can be extracted and purified by any methods known to those skilled in the art and can then be stabilized and formulated according to the procedures of this invention. Any recombinant β-HIFN or IL-2 protein that has been extracted and partially or completely purified can be formulated according to the procedures of this invention. For example, the methods of culturing *E. coli* transformed to produce β-HIFN, extracting and purifying the recombinant β-HIFN as described in U.S. Pat. No. 4,462,940 are herein incorporated by reference. The extraction and purification procedures disclosed and exemplified herein are the most effective and efficient methods known to the inventors.

The carrier medium used for the formulations of this invention, which are suitable for therapeutic or clinical administration, may be any non-toxic, inert and aqueous-based vehicle such as those commonly used to formulate pharmaceuticals for animal or human administration. The carrier also is selected so that it does not affect the biological activity of the lipophilic protein. Examples of such carriers include distilled water, physiological saline, Ringer's solution, dextrose solution, and Hank's solution. The same carriers can be used to reconstitute lyophilized lipophilic protein.

The present invention is further described by the following examples. These examples are provided for purposes of illustration only and are not intended to limit the invention in any manner. In the examples all parts and percentages are by weight if solids and by volume if liquids, unless otherwise specified, and all temperatures are in degrees Celsius.

EXAMPLE 1

An analog IFN-β designated IFN-$β_{ser17}$ was recovered from *E. coli*. The amino acid sequence of this recombinant IFN-β is different from that of native human IFN-β in that the cysteine at position 17 has been changed to serine. The strain of IFN-$β_{ser17}$-producing *E. coli* (K12/MM294-1) carrying plasmid pSY2501 used in this example was deposited at the American Type Culture Collection on Nov. 18, 1983 under accession number 39,517. Said analog is described in U.S. Pat. Nos. 4,518,584 and 4,588,585 assigned to Cetus Corporation.

The *E. coli* thus transformed were grown in a 1000-liter fermentor at 37° C. The dissolved oxygen was maintained at about 40% by, as necessary; (1) increasing agitation; (2) adding air; and (3) adding oxygen.

Once the fermenter was filled with water to the operating volume, the following trace elements were added:

| | |
|---|---|
| ZnSO$_4$ . 7H$_2$O | 72 µM |
| MnSO$_4$ . 4H$_2$O | 30 µM |
| CuSO$_4$ . 5H$_2$O | 3 µM |
| Na$_3$ citrate 2H$_2$O | 1.5 mM |
| KH$_2$PO$_4$ | 21 mM |
| (NH$_4$)$_2$SO$_4$ | 72 mM |

The fermenter feed and addition vessels were then sterilized according to standard operating procedures. Then the following sterile additions were made:

| | |
|---|---|
| MgSO$_4$ . 7H$_2$O | 20 mM |
| FeSO$_4$ . 7H$_2$O | 100 µM |
| L-tryptophan | 70 mg/L |
| thiamine . HCl | 20 mg/L |
| glucose | 5 g/L |

The fermenter was cooled and inoculated with frozen or seed *E. coli* culture at 2 mg/L. A glucose feed was employed to maintain the glucose concentration between 5–10 g/L. At approximately 15 hours after fermentation was begun, the pH was adjusted with KOH to 6.8. Optical density measurements and residual glucose measurements on samples were taken at 14–16 hours and approximately one hour intervals thereafter.

Induction of IFN-$\beta_{ser17}$ production by depletion of L-tryptophan from the culture medium occurred at about OD$_{680}$=10 followed by the addition of casamino acids to a final concentration of 2% at OD$_{680}$=15. The cultures were harvested when glucose consumption reached 40±6 g/l.

The refractile bodies containing the IFN-$\beta_{ser17}$ protein were then isolated. The harvested material was concentrated about 5–10 fold by circulating the harvest material under pressure through UF cross-flow filtration cartridges with a 100K molecular weight cutoff. Cells were disrupted by 3 passes through a Manton-Gaulin high-pressure homogenizer at 6,000 to 8,000 psig.

EDTA was added to the disruptate to a final concentration of 5 mM. The suspension was then diafiltered against 5 volumes of deionized water.

EDTA was then added to a final concentration of 2 mM. Octanol was added to 1% (v/v) to kill any residual live bacteria in the diafiltered product. The suspension was redisrupted by passing it twice through the Manton-Gaulin high-pressure homogenizer at 6,000–8,000 psig.

Sucrose was added to the redisruptate to a final concentration of 23% (wt/wt), creating a final density of between 1.1 and 1.25 g/ml. The mixture was centrifuged at 10,000 to 15,000 xg, and the particle pellet or paste was collected. A temperature of at least 20° C. was maintained prior to and during centrifugation.

The particle pellet was then solubilized in phosphate buffered saline with 2% SDS. Solid DTT and EDTA were added to a final concentration of 10 mM and 2 mM, respectively. At a pH of about 9, the suspension was heated to 50°±5° C. for 10 minutes under nitrogen. The reaction mixture was then cooled to approximately 25° C., and then the pH of the mixture was adjusted to 7.4.

A volume of 2-butanol equal to the total volume of the suspension was measured. The suspension and organic solution were pumped separately but simultaneously at flow rates of 1.1 to 1.3 liters per minute through a static mixer and then into a continuous centrifuge (Westfalia at approximately 11,770 xg) for phase separation. The 2-butanol-rich phase containing the IFN-$\beta_{ser17}$ was collected (Organic Extract).

The 2-butanol extract was mixed with 2.5 volumes of 0.1% SDS in phosphate-buffered saline. Solid DTT was added to a final concentration of 2 mM. The pH of the organic extract/buffer solutions was adjusted to 6.2±0.1 with glacial acetic acid (Acid Precipitate).

The mixture was then centrifuged (Sharples centrifuge at 13,200 xg) for approximately 2–6 hours. The supernatant was decanted and the final pellet was then collected (Final Pellet) containing approximately 81% IFN-$\beta$.

The final pellet was then re-suspended with 5% SDS in 50 mM phosphate buffer and 5 mM EDTA. Solid DTT was added to a final concentration of 20 mM, and the pH was adjusted to 8.5 with NaOH. The suspension was heated to 50°±5° C. for 10 minutes under nitrogen, and then cooled to approximately 25° C. The pH was then adjusted to a pH of 5.5 with glacial acetic acid, and the solution was filtered through a 0.65 µm filter.

The filtrate was then processed by pre-column chromatography by loading a Sephacryl® S200 column and collecting fractions into clean, depyrogenated vessels using an elution buffer that is composed of 50 mM acetate, pH 5.5, 1 mM EDTA and 1% SDS. The fractions containing the IFN-$\beta$ monomer were pooled.

The pre-column pool was then concentrated by using a hollow-fiber ultrafiltration unit with a 10K molecular weight cut-off.

The concentrated pre-column pool was then oxidized using o-iodosobenzoic acid (IBA). The oxidation was effected by adding equimolar amounts of protein and IBA into a reaction vessel containing 2 mM sodium pyrophosphate, 0.1% SDS and 1 mM EDTA. A 20 µM excess of IBA was present at the end of the oxidation. The pH was controlled at 9.0±0.1 with NaOH during oxidation, and adjusted to 5.5±0.2 with glacial acetic acid when the oxidation was completed.

The IFN-$\beta$ protein was then concentrated using a hollow-fiber ultrafiltration unit with a 10K molecular weight cut-off.

The protein was then loaded onto the main column (Sephacryl® S200), and fractions were collected into clean, depyrogenated vessels using an elution buffer that is composed of 50 mM acetate, pH 5.5, 1 mM EDTA and 0.1% SDS.

A SDS-PAGE was performed on samples from each fraction tube starting from the beginning of the peak to be pooled to the end of the peak. Using the SDS-PAGE results, the fractions containing no high molecular weight contaminants were determined. Those fractions were then pooled.

The main column pool was then concentrated by using a hollow-fiber ultrafiltration unit with a 10K molecular weight cut-off.

The above procedure performed with the main column was repeated on a Sephadex® G-75 column. Using the SDS-PAGE results, the fractions containing neither low nor high molecular weight contaminants were pooled.

The desalting step was then performed wherein 0.1% sodium laurate was used as a tranfer component as follows. The pH was adjusted with an appropriate basic agent, such as 1 mM NaOH.

A Sephadex® G-25 column was then equilibrated with an elution buffer of degassed 0.1% sodium laurate in 10 mM disodium phosphate at pH 9–9.2 and loaded with the Sephadex® G-75 pool containing 0.1% SDS adjusted to pH 9.0. The recombinant $\beta$-HIFN is chromatographed over the G-25 column at low flow rates and low loads.

The desalted peak is collected using ultraviolet absorbance detection at $A^{280}$. The pH of the G-25 pool is then adjusted to pH 3 with 1.0N HCl. The sodium laurate precipitates from the acidic solution. To remove the precipitated sodium laurate, the mixture was centrifuged at 35,000 xg for 30 minutes, and the supernatant was then filtered through a 0.45 micron nitrocellulose filter.

The amounts of normal serum albumin (NSA) and β-HIFN are then calculated to reach a final concentration of 2.5% NSA and 0.25 mg/ml β-HIFN. The pH of the NSA is then adjusted to 3 to 3.2, and the requisite amount of NSA is then combined with the β-HIFN. Such combination is incubated at pH 3 to 3.2 for from 5 to 15 minutes. Then the pH is raised to 7.2 to 7.8 by adding sodium hydroxide.

The neutralized product then undergoes pre-filtration through a 0.45-micron nitrocellulose filter, and then sterile filtration through a 0.22 micro nitrocellulose filter.

Immediately after the neutralization and filtration procedures, the correct dosage amounts of the IFN-$\beta_{ser17}$, (0.25 mg containing approximately $0.5 \times 10^8$ units), are aseptically filled into sterilized vials with sterilized stoppers under sanitary and sterile conditions that are carefully monitored. The vials are then quickly placed into a lyophilizer where appropriate thermocouples are attached. The vials are frozen to between −35° and −45° C. When the lyophilization cycle is completed, the vials are mechanically sealed under a vacuum.

EXAMPLE 2

An analog IL-2 designated des-ala-IL-$2_{ser}$125 was recovered from *E. coli*. The amino acid sequence of this recombinant IL-2 differs from that of native human IL-2 by the absence of the initial N-terminal alanine residue and by the substitution of a serine for a cysteine at position 125. The strain of des-ala-IL-$2_{ser125}$-producing *E. coli* (K12/MM294-1) carrying plasmid pLW45 used in this example was deposited at the American Type Culture Collection on Mar. 4, 1984 under accession number 39,626. Said analog is disclosed in U.S. Pat. No. 4,530,787 to Shaked et al. and prepared by the methods disclosed in U.S. Pat. Nos. 4,518,584 and 4,588,585 assigned to Cetus Corporation.

The *E. coli* transformed with plasmid LW45 are grown essentially as described in Example 1 for the *E. coli* transformed with pSY2501 with the following modifications. Only 30 μM rather than 72 μM of $ZnSO_4 \cdot 7H_2O$ are initally added as a trace element to the fermenter. Only 3 mM rather than 20 mM $MgSO_4 \cdot 7H_2O$, 72 μM rather than 100 μM $FeSO_4 \cdot 7H_2O$, and 5 mg/L tetracycline rather than no tetracycline are then added under sterile conditions.

After sucrose is added to the redisruptate, and the mixture centrifuged according to the procedures of Example 1, the particle pellet is solubilized in 5% rather than 2% SDS in phosphate buffered saline. The solubilized refractile material is then centrifuged at 25,000–35,000 xg.

The reduction step is essentially the same as described in Example 1, except that the pH is most preferably at about 8.5 rather than about 9.0, there is a final concentration of 50 mM rather than 10 mM DTT, and 5% SDS rather than 2% SDS is used.

Following the reduction step, instead of the next step being an organic extraction as in the β-HIFN process, the reaction mixture is cooled to about 25° C., and the pH is readjusted to 5.5±0.1 using glacial acetic acid.

Chromatographic separation of the higher molecular weight contaminants is achieved using a Sephacryl® S-200 column. The solubilized and reduced refractile body protein is loaded onto the column and fractions are collected into clean, depyrogenated vessels using an elution buffer containing 50 mM acetate pH 5.5, 1 mM EDTA and 0.1% SDS.

Peak fractions (those falling within 70% of the maximum peak height) are pooled and subjected to a controlled oxidation as follows:

The S200 pool is oxygenated by bubbling air through the solution, and the oxidation is intiated by adding $CuCl_2$ in a molar ratio of 1:3 ($CuCl_2$ to IL-2 protein). The oxidation is carried out at about 25° C. in 50 mM phosphate buffered saline. The pH is controlled at 7.0±0.2 during oxidation and adjusted to 5.5±0.2 when the oxidation is completed. Since oxidized IL-2 is more hydrophilic than reduced IL-2, the progress of the oxidation reaction is monitored by RP-HPLC.

The oxidized IL-2 is then concentrated using a hollow fiber ultrafiltration unit with a 10,000 molecular weight cutoff. The pH of the oxidized pool is then adjusted to pH of about 2 to about 3 and filtered through a 0.45 μM nitrocellulose filter.

Preparative HPLC using a Vydac® $C_4$ bonded phase silica gel column supplied with two solvents is the next step in the IL-2 purification scheme. Solvent 1 is 6% acetic acid and 10% 2-propanol in distilled water, and solvent 2 is 6% acetic acid and 94% 2-propanol. After pumping solvent 1 for 30 minutes, the acidified IL-2 protein is loaded. The column is developed with a gradient of solvents 1 and 2 and the protein which elutes at about 40% solvent 2 is pooled into a depyrogenated graduated cylinder.

In a 1:1 (volume to volume) ratio, 0.8N NaOH is then added to the pooled protein, causing the protein to precipitate. The precipitated protein is then solubilized in 0.1M $Na_2HPO_4$ with 1% SDS.

The final chromatographic step in the purification of IL-2 involves a second Sephacryl® S-200 column. The primary objective of this column is to separate the IL-2 monomer fractions from higher molecular weight oligomers of the protein. The column is eluted with buffer containing 50 mM acetate pH 5.5, 1 mM EDTA and 0.1% SDS, and IL-2 monomer fractions are pooled.

Immediately preceding formulation, the IL-2 protein is diafiltered at a pH range of from 9–9.2 against 10 mM disodium phosphate containing 0.1% sodium laurate as a transfer component. The pH of the diafiltrate is adjusted to 3 with HCl (1–3M). The sodium laurate precipitates, but the IL-2 remains in solution.

The mixture is then centrifuged at 35,000 xg for 30 minutes, and the supernatant is filtered through a 0.22 micron nitrocellulose filter.

The filtered supernatant is then formulated by adding 2.5% normal serum albumin, and the mixture is incubated at a pH of about 3 to 3.2 for from about 5 to 15 minutes.

The pH of the solution is then raised to physiologic pH with NaOH. The formulated solution is then pre-filtered through a 0.45 μM filter and sterile filtered through a 0.22 μM filter. Finally, the product is lyophilized to dryness in a container vial for storage at 4° C. as described in Example 1.

EXAMPLE 3

The extraction and purification procedures for recombinant IFN-β were essentially performed as described in Example 1 up to the point of the desalting step. At which point, the following alternative formulation processes were performed.

PPF Formulation

A total of 22 ml of IFN-β from the G-75 pool (1.3 mg/ml of IFN-β) was loaded on a desalting G25 Sephadex column equilibrated with a pH 11 buffer. A total of 4.46 ml of 2.2% plasma protein fraction (PPF) was adjusted to pH 3 and added to 5.56 ml of the desalted IFN-β at pH 3, containing 0.25 mg/ml IFN-β. PPF is derived from Cohn Fraction $IV_1$. PPF is similar to HSA with the exception that PPF has more α- and β- globulins. Fraction $IV_1$ has the highest amount of α and β globulins. The IFN-β and PPF mixture was incubated for about 45 minutes and then adjusted to pH 7.5.

II. PPF/HSA Formulations

A total of 30 ml of the G-75 IFN-β pool above was concentrated to 10.5 ml and the pH was adjusted to 11. The concentrate was desalted on a G25 Sephadex column fully equilibrated to pH 11. The IFN desalted pool was used in the following experiments.

A total of 3.33 ml of the desalted IFN-β having 0.25 mg IFN per ml was used in each experiment. The appropriate protein stabilizer, either HSA or PPF, in an amount sufficient to reach the respective concentrations indicated in the second column of the table, just below, was in each case adjusted to pH 3 and mixed with the IFNβ. The mixture was then incubated, for the intervals noted in the Table, at pH 3, and then the pH was raised to between 7.3 and 7.5. The results are indicated as follows:

| Stabilizer | Amount of Stabilizer (%) | Incubation Time (min.) | Clarity at pH 7.3–7.5 |
|---|---|---|---|
| HSA | 2.5 | 45 | slightly hazy |
| HSA | 5.0 | 45 | very clear |
| HSA | 2.5 | 15 | slightly hazy |
| HSA | 5.0 | 15 | very clear |
| PPF | 2.5 | 45 | very clear |
| PPF | 2.5 | 15 | very clear |

The PPF formulations were found, when examined visually, to have the best clarity, with 5.0% HSA next best, followed by 2.5% HSA. When each formulation was lyophilized and reconstituted with water, the PPF formulations reconstituted more clearly than the HSA formulations. All lyophilized formulations had IFN-β activity.

Experiments done at pH 3–4 without an incubation period appeared to show no appreciable difference from those that underwent an incubation period. Changes in concentration of PPF do result, however, in a marked difference in clarity.

EXAMPLE 4

Figure 1:
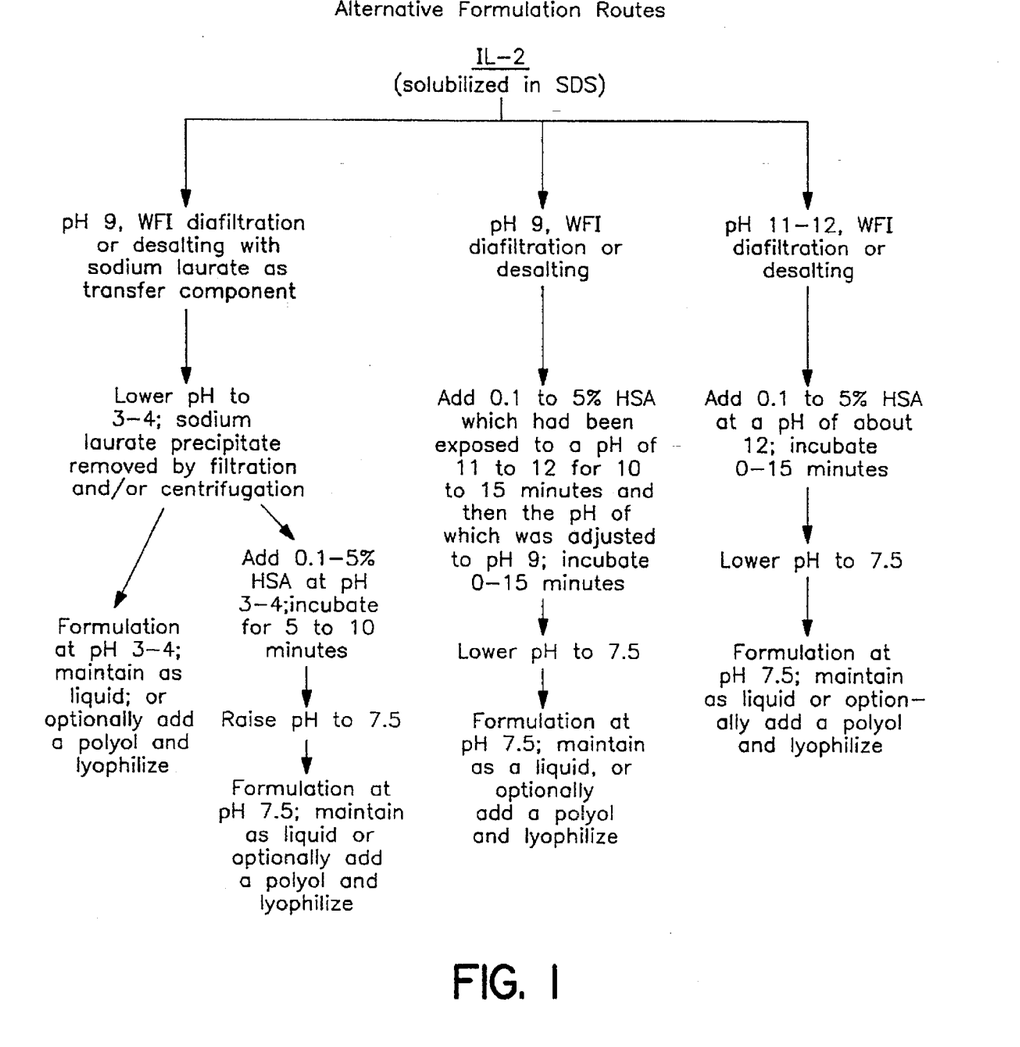
FIG. 1 outlines preferred embodiments of alternative formulation routes for recombinant IL-2. The bifurcated formulation route on the left side wherein a transfer component is used during desalting or diafiltration, as well as the high pH formulation route on the right side of FIG. 1, also provide preferred embodiments for formulating recombinant HIFN-β; however, in both alternatives, protein plasma fraction (PPF) rather than human serum albumin (HSA) is the more preferred protein stabilizer for recombinant HIFN-β.

This example basically outlines the high pH formulation route for recombinant IL-2 as shown schematically in the formulation route on the right-hand side of FIG. 1.

Recombinant des-ala-IL-$2_{ser}$125 is extracted and purified according to Example 2 up to the diafiltration step that immediately precedes the formulation procedure. Instead of the S200 column pool being diafiltered at a pH range of 9–9.2 employing a transfer component, the IL-2 pool is diafiltered at pH 11–12 without a transfer component against water suitable for injection (WFI) with a low ionic strength buffer the pH thereof adjusted to 12 with NaOH. Human serum albumin (HSA), 1.25% which has been adjusted to a pH of about 12 is combined with the diafiltered IL-2 pool. The mixture is incubated for about five minutes.

The pH is then lowered with 1M HCl to pH 7.5. The formulation is then pre-filtered, sterile filtered and lyophilized according to the procedures of Example 2.

EXAMPLE 5

This example basically outlines the pH 9 formulation route shown schematically as the middle route of FIG. 1.

The procedures of Example 2 are followed up to the point of the diafiltration step immediately preceding the formulation procedure. Instead of diafiltration being carried out with a transfer component, the S200 column pool is diafiltered at a pH of about 9 against water suitable for injection (WFI) with a low ionic strength buffer the pH of which is adjusted to 12 with NaOH.

Human serum albumin (HSA), 1.25%, which has been exposed to a pH range of about 11–12 for 10 to 15 minutes and adjusted to approximately pH 9 is added to the diafiltrate.

The formulation at pH 9 is then pre-filtered, sterile filtered and lyophilized according to the procedures of Example 2. Alternatively, the pH of the formulation can be lowered with an appropriate acidic agent to pH 7.2 to 7.6, and then pre- and sterile filtered and lyophilized.

EXAMPLE 6

In both isothermal and nonisothermal elevated temperature studies, increasing the level of human serum albumin in a representative formulation of this invention results in increased thermal stability. Multiple isothermal stability (MIS) studies and linear nonisothermal stability (LNS) studies were used both to compare different formulations and to predict the stability of HIFN-β formulations representative of those of this invention, specifically those formulations comprising IFN-$β_{ser17}$ and human serum albumin (HSA).

The following lyophilized recombinant IFN-$β_{ser17}$ formulations with human serum albumin and dextrose were prepared according to the processes of this invention.

| Formulation | Vial Contents (mg/vial) | | |
|---|---|---|---|
| | IFN-$β_{ser17}$ | HSA | Dextrose |
| 1 | 0.06 | 15 | 15 |
| 2 | 0.30 | 15 | 15 |
| 3 | 1.20 | 60 | 15 |

The lyophilized product was reconstituted with 1.2 ml of sterile water, prior to bioassay. IFN-$β_{ser17}$ has a nominal specific activity of $1.8 \times 10^8$ IU/mg interferon-β. Bioassay was performed according to a yield reduction assay essentially as described in Steward et al., *J. Virol.*, 6: 795–799 (1970). Vials of each of the representative formulations were placed in the following environments:

(A) in a controlled-temperature refrigerator (2°–8° C.);

(B) in controlled-temperature incubators set at 25°, 37°, 55°, 75° and 80° C. (for MIS studies); and (C) in a heating water circulator controlled by a microprocessor-based temperature programmer (Lauda Model No. KP-20D) wherein the temperature was raised from 50° C. to 80° C. at a 1.5° C./hour linear rise (for LNS studies).

At set time intervals, a specified number of vials of each formulation were removed, reconstituted and submitted for bioassay. Specifically for the LNS studies of (C), the vials were removed at 0 (50° C.), 13.5 hours (70° C.), 16.5 hours (75° C.) and 20 hours (80° C.).

The potency stability studies of the vials under extended storage at 2°–8° C. (A) showed no statistically significant changes in potency of any of the formulations over a two-year time period.

Arrhenius plots for the three formulations based on the MIS studies over 3 months (B) predicted, on the basis of the Arrhenius equation, a 10% decrease in potency after 3 years of storage under refrigeration for formulations 1 and 2 whereas it was predicted that such a potency loss for formulation 3 would take at least 10 years.

LNS studies (C), established as a screening test for comparing interferon formulations [Sedmak et al., *Methods Enzymol.* 78A: 591–595 (1981); Jameson et al., *Cryobiology* 16: 301–314 (1979)], because of large bioassay variability cannot accurately predict the long-term stability of a given formulation but are useful to compare the relative stability of different formulations. Such MIS studies have an advantage in being able to be and can be performed in a matter of days. Consistent with the MIS results, formulation 3 was predicted to be more thermally stable than the other two formulations. The LNS studies further indicated that formulation 2 would be more thermally stable than formulation 1.

EXAMPLE 7

Des-ala-IL-$2_{ser}$125 was extracted and purified essentially as described in Example 2 up to the point of running the pool through the second Sephacryl® S200 column. The S200 pool was loaded onto a 2.6 cm×100 cm Sephadex G-100 column, which was eluted as described above using 0.1% w/v SDS. The fractions were analysed by SDS/Page, and the parent fractions pooled. These purest fractions contained 95–98% pure IL-2 with 0.2–0.5 ng of endotoxin per 100,000 units. Over 30% of the IL-2 present in the crude lysate was recovered as pure IL-2.

When stored at 4° C. under nitrogen, these pooled G-100 fractions were found to be stable for at least six weeks without additions. An SDS-containing precipitate formed at 4° C. which could be redissolved at 25° C. prior to use or could be removed without significant loss of IL-2 units.

The purified, fully reduced product obtained as described above was oxidized using iodosobenzoic acid, as described above, resuspended, and run on an HPLC column using propanol-trifluoroacetic acid. Formulations were made from the HPLC pool.

I. Low pH Treated Mannitol and HSA Formulations

The HPLC pool was then diluted 10-fold into Buffer K (50 mM acetate, 1 mM EDTA and 0.1% SDS), concentrated and diafiltered versus the same buffer. About 30 mg of the diafiltrate was concentrated and diafiltered versus 10 mM Tris.HCl at pH 9.2. Ten mg of this diafiltrate was loaded on a G-25 desalting column to remove SDS to a level of 0.65 μg/mg. Sufficient acid was added to the G-25 pool to reduce its pH to 3, and it was split into three portions. To the respective portions were added sufficient amounts of stabilizer to yield the following final formulation concentrations: 5% (w/v) mannitol, 1.25% (w/v) human serum albumin (HSA), and 2.5% (w/v) HSA.

The 2.5% HSA formulation was split into two portions, one of which was incubated for 30 minutes and one of which was incubated for 60 minutes. Both 2.5% HSA samples were clear after incubation. The pH of both was raised to 7.5 with 2.5N NaOH with no change in the clarity, indicating solubility.

A. Low pH Treated HSA Formulation

The above HSA formulation experiment was prepared in a larger volume to test visual clarity. The same IL-2 in Tris HCl at pH 9.2 was then concentrated and loaded on a desalting G25 Sephadex column. To a total of 49.6 ml IL-2 from the desalted pool (60 ml final volume) was added 100 μl of 6N HCl to adjust the pH to 2.58. To 5.9 ml of 2.5% HSA and 4.5 ml H$_2$O was added dropwise concentrated HCl to a pH of 3. The IL-2 solution was incubated with the albumin solution for 15 minutes at pH 3, and then the pH was raised with 2.5N NaOH to 7.5. The solution was clear, indicating that the IL-2 dissolved in the solution at physiological pH. After lyophilization and reconstitution with water the sample remained clear.

It is apparent that this method of desalting removes considerable SDS. Increasing the HSA concentration from 1.25 to 2.5% resulted in considerable improvement in solubility at physiological conditions, indicating that higher concentrations of stabilizer are preferred for low pH treatments whereas for the higher pH treatment, above pH 10, 1.25% HSA results in very good solubilization.

B. Low pH Treated Mannitol Formulation

A mannitol IL-2 formulation was prepared by mixing 49.6 ml of the G-25 desalted IL-2 pool described just above in Section A with 15 ml of 25% mannitol and adjusting the pH of the mixture down to 3.0 with HCl. The final concentration of mannitol was 2.5% (w/v). After lyophilization and reconstitution with water the sample remained clear at pH 3.0.

This example illustrates that the stabilizers herein can be used to stabilize the formulation at a low pH of 2–4 if the pH is maintained at 2–4 and lyophilized at pH 2–4. If the pH is raised above 4, however, the carbohydrate stabilizers such as mannitol will not act to solubilize the lipophilic protein. Only the protein stabilizers such as HSA will solubilize the protein as the pH is raised to physiological pH.

II. Low pH Treated PPF Formulation

The same desalted IL-2 pool as used above for HSA formulation was employed containing 1 mg/ml IL-2 at pH 9.2. When 7.5 ml PPF (5%) and 2.5 ml of 1 mg/ml of the desalted IL-2 were mixed, the mixture had a pH of 7.6 and was clear at first, but within two minutes turned hazy. When the pH of the mixture was dropped to 2.3 after 15 minutes, it was clear and remained clear when the pH was readjusted to 7.5.

In a second case, the pH of 7.5 ml of 5% PPF was adjusted to 9.2, and Tris HCl at pH 8.8 was added (0.05 μl of 1.5M). A total of 2.5 ml of 1 mg/ml desalted IL-2 as described above was added and the mixture was incubated for 15 minutes at pH 9.2. When the pH was dropped to 7.6, the solution was clear, but after one minute it began to turn slightly hazy.

In a third case, when the pH of the 5% PPF was lowered to 3.1, IL-2 at pH 3.3 was added, the mixture was adjusted to pH 3.1 with dropwise concentrated HCl, the mixture was incubated for 15 minutes, and the pH was raised with 2.5N NaOH, the resulting solution was as clear as the control formulation (3.75% PPF alone).

Comparison of formulations with 2.5% HSA, 2.5% PPF, 0.5% HSA and 0.5% PPF (w/v) under identical conditions revealed that HSA formulations are clearer than PPF formulations, but both types of formulations are acceptably clear, indicating suitable solubility.

The low pH formulation was found not to be as soluble as the pH 12 formulation. Experiments to optimize the pH 3 formulation revealed that 5% HSA was distinctly better than the 2.5% HSA formulation. Also, increasing the incubation time from 15 minutes to 60 minutes assisted the solubility. The 5% HSA at 15 minutes incubation, however, was found to be better than the 2.5% HSA at 60 minutes incubation.

The above results indicate that for IFN-β, PPF is a better stabilizer than HSA, whereas for IL-2, HSA is a better stabilizer than PPF. In addition, tests for biological activity of representative formulated proteins at pH 3 revealed that the proteins were biologically active.

Conclusion

The process and compositions of the present invention as described herein yield lipophilic protein preparations which are of relatively high purity, with residual SDS levels of less than about 10 p.p.m. and which may be formulated into therapeutically acceptable preparations in a non-toxic, inert, physiologically compatible carrier medium for clinical and therapeutic uses. The instant invention provides alternative lipophilic protein formulation routes for pharmaceutical compositions with levels of SDS reduced to about 2–20 p.p.m., preferably to less than about 10 p.p.m., and more preferably to about 2–6 p.p.m. Although the preferred embodiments described relate to β-HIFN and IL-2 specifically, the purification methods of the instant invention can be used to purify other proteins with lipophilic characteristics similar to β-HIFN and IL-2.

Further, the instant invention provides for alternative formulation routes that avoid extremely high pH ranges.

The foregoing description of the preferred embodiments of the instant invention has been presented for purposes of illustration and description. It is not intended to be exhaustive or to limit the invention to the precise form disclosed, and obviously many modifications and variations are possible in light of the above teaching. The particular embodiments were chosen and described to explain best the principles of the invention and its practical application thereby to enable others skilled in the art to utilize best the invention in various embodiments and with various modifications as are suited to the particular use contemplated. It is intended that the scope of the invention be defined by the claims appended hereto.

DEPOSITS

The following cultures were indicated as being deposited at the American Type Culture Collection (ATCC), 12301 Parklawn Drive, Rockville, Md. 20852 (USA) at the beginning of Example 1 and Example 2, respectively:

| Culture | ATCC Accession No. | Deposit Date |
|---|---|---|
| E. coli (K12/MM294-1) carrying pSY2501 | 39,517 | November 18, 1983 |
| E. coli (K12/MM294-1) carrying pLw45 | 39,626 | March 4, 1984 |

Said deposits were made pursuant to a contract between the ATCC and the assignee of this patent application, Cetus Corporation. The contract with the ATCC provides for permanent availability of said strains and progeny thereof to the public upon issuance of a U.S. patent related to this application describing and identifying the deposits or upon the publication or laying open to the public of any U.S. or foreign patent application, whichever comes first, and for the availability of the strains and the progeny thereof to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the strains on deposit should die or be lost or destroyed when cultivated under suitable conditions, they will be promptly replaced upon notification with a viable culture of the same strain.

The deposits under the terms of the Budapest Treaty assure that said cultures deposited will be maintained in a viable and uncontaminated condition for a period of at least five years after the most recent request for the furnishing of a sample of the deposited microorganisms was received by the ATCC and, in any case, for a period of at least 30 years after the date of the deposit.

Availability of the deposited strains is not to be construed as a license to practice the invention in contravention of the rights granted under the authority of any government in accordance with its patent laws.

Also, the present invention is not to be considered limited in scope by the strains deposited, since the deposited embodiments are intended only to be illustrative of particular aspects of the invention. Any microorganism strains which are functionally equivalent to those deposited are considered to be within the scope of this invention. Further, various modifications of the invention in addition to those shown and described herein apparent to those skilled in the art from the preceding description are considered to fall within the scope of the appended claims.

What is claimed is:

1. A process for formulating a lipophilic protein selected from an unglycosylated recombinant human interferon-β (IFN-β) and an unglycosylated recombinant human interleukin-2 (IL-2) that has been recovered from a bacterial host transformed to produce it wherein the cell wall and cell membrane of the host was disrupted and the protein in the disruptate was isolated and purified up to the point of final diafiltration or desalting, comprising the steps of (a) diafiltering or desalting said lipophilic protein at a pH range of about 8.5 to 10.0 employing a low ionic strength elution buffer containing a transfer component;

(b) lowering the pH of the diafiltrate or desalted pool with an appropriate acid agent to a pH from about 2 to about 4; and (c) removing the precipitated transfer component by centrifugation and/or filtration.

2. A process according to claim 1 further comprising the steps of:

(d) adding to the protein pool a carbohydrate stabilizer; and (e) lyophilizing the resulting composition at the pH range of about 2 to about 4.

3. A process according to claim 1 further comprising the steps of:

(d) adding to the protein pool a stabilizer for the protein which has previously been adjusted to a pH of about 2 to about 4;

(e) incubating the mixture at said pH range of about 2 to about 4 from about five to forty-five minutes; and (f) raising the pH of the protein solution to 6.8 to 7.8 with an appropriate basic agent.

4. A process according to claim 3 further comprising the steps of:

(g) lyophilizing the protein composition at the pH range of 6.8 to 7.8; and (h) optionally reconstituting said lyophilized composition.

5. A process according to claim 4 wherein the protein stabilizer is HSA or PPF, the pH range for step (a) is 9 to 9.5;

the pH range for steps (b) and (d) is 3 to 4; and the pH range for steps (f) and (g) is 7.2 to 7.6.

6. A process according to claim 5 wherein the pH range for step (a) is 9 to 9.2; the pH for steps (b) and (d) is about 3.5 and the pH for steps (f) and (g) is about 7.5.

7. A process according to claim 3 further comprising the steps of:

(g) adding a polyol to the protein solution;

(h) pre-filtering and sterile filtering the solution;

(i) lyophilizing the solution; and (j) optionally reconstituting said lyophilized composition.

8. A process according to claim 7 wherein the protein stabilizer is HSA or PPF, and wherein the polyol is mannitol or dextrose.

9. A process according to claim 3 wherein the stabilizer is human serum albumin or human plasma protein fraction, and the protein is IL-2 or β-HIFN.

10. A process according to claim 4 wherein the protein is IL-2 and the stabilizer is human serum albumin.

11. A process according to claim 4 wherein the protein is β-HIFN and the stabilizer is human plasma protein fraction.

12. A process according to claim 11 wherein the β-HIFN is IFN-$β_{ser17}$.

13. A process according to claim 4 wherein the transfer component of step (a) is at a concentration range of 0.5 to about 2% and is selected from the group co, rising a fatty acid salt having 10 to 13 carbon atoms, urea at a concentration of 5–7M, or guanidine hydrochloride at a concentration of 5–7M.

14. A process according to claim 13 wherein the transfer component is at a concentration range of about 0.1% to about 1% and is a laurate salt.

15. A process according to claim 14 wherein said laurate salt is sodium laurate.

16. A process according to claim 4 wherein the mixture is incubated at pH 3 to 4 for about five to 15 minutes.

17. A process of claim 2 wherein the carbohydrate stabilizer is mannitol or dextrose.

18. A process of claim 1, wherein the recombinant human IFN-β is IFN-$β_{ser17}$.

19. A process for formulating a lipophilic protein selected from an unglycosylated recombinant human interferon-β (IFN-β) and an unglycosylated recombinant human interleukin-2 (IL-2) that has been recovered from a bacterial host transformed to produce it wherein the cell wall and cell membrane of the host was disrupted and the protein in the disruptate was isolated and purified, comprising the steps of:

(a) adjusting the pH of the medium in which the protein is contained to about 2 to 4;

(b) adding to the protein medium a stabilizer for the protein which has been previously adjusted to a pH of about 2 to 4; and (c) lyophilizing the resulting composition at about pH 2 to 4, wherein the recombinant human IFN-β is IFN-$β_{ser17}$.

20. A process for formulating a lipophilic protein selected from an unglycosylated recombinant human interferon-β (IFN-β) and an unglycosylated recombinant human interleukin-2 (IL-2), isolated from a bacterial host transformed to produce it and purified comprising the steps of (a) adjusting the pH of the medium in which the lipophilic protein is contained to about 2 to 4;

(b) adding to the protein medium a protein stabilizer for the lipophilic protein which has been previously adjusted to a pH of about 2 to 4; and (c) raising the pH of the resulting composition to 6.8 to 7.8, wherein the recombinant human IFN-β is IFN-$β_{ser17}$.

21. A process for formulating a lipophilic protein selected from an unglycosylated recombinant human interferon-β (IFN-β) and an unglycosylated recombinant human interleukin-2 (IL-2) which has been extracted and isolated from a bacterial host transformed to produce it and purified, comprising the steps of (a) combining the protein with a protein stabilizer and adjusting the pH of the combination to about 2 to 4; and (b) raising the pH of the resulting composition to 6.8 to 7.8, wherein the recombinant human IFN-β is IFN-$β_{ser17}$.

* * * * *